(12) United States Patent
Palle et al.

(10) Patent No.: US 6,269,321 B1
(45) Date of Patent: Jul. 31, 2001

(54) METHOD FOR OPTIMIZING MECHANICAL STRENGTH OF A CASTING USING MICROSTRUCTURE PREDICTIONS

(75) Inventors: Nagendra Palle, Ann Arbor; Ravi Vijayaraghavan, Farmington Hills; Jacob Wesley Zindel, Ann Arbor; William Thomas Donlon, Dearborn; John Edmond Allison, Ann Arbor, all of MI (US)

(73) Assignee: Ford Global Technologies, Inc, Dearborn, MI (US)

( * ) Notice: Subject to any disclaimer, the term of this patent is extended or adjusted under 35 U.S.C. 154(b) by 0 days.

(21) Appl. No.: 09/150,690

(22) Filed: Sep. 10, 1998

(51) Int. Cl.[7] .............................. B22D 27/00; G01N 17/00
(52) U.S. Cl. .............................. 702/136; 702/23; 702/27; 702/30; 164/4.1; 164/57.1; 164/151.4
(58) Field of Search .............................. 702/136, 23, 27, 702/30; 73/87, 104; 164/4.1, 151.4, 57.1; 703/12

(56) References Cited

U.S. PATENT DOCUMENTS

| | | | |
|---|---|---|---|
| H633 * | 6/1989 | McLellan | 73/87 |
| 4,381,666 * | 5/1983 | Feiertag et al. | 73/87 |
| 4,598,754 * | 7/1986 | Yen et al. | 164/4.1 |

* cited by examiner

Primary Examiner—Kamini Shah
Assistant Examiner—Hien Vo
(74) Attorney, Agent, or Firm—Roger L. May; Damain Porcari

(57) ABSTRACT

A method for quantitatively predicting and consequently minimizing the amount of critical phases such as eutectic $Al_2Cu$ formed during solidification of Al—Si—Cu alloys used in a vehicle engine component comprises developing a micromodel to simulate microstructure evolution in cast Al—Si or Al—Cu alloys. The micromodel is calibrated using experimental thermal analysis cooling curves and an optimization process. Microstructure evolution and cooling curves are simulated for a casting using the calibrated micromodel. Precipitation of critical phases such as $Al_2Cu$ in the casting is predicted as a function of solidification conditions. The model allows casting process variables to be varied with predictable results so that the casting process can be controlled via the micromodel.

19 Claims, 15 Drawing Sheets

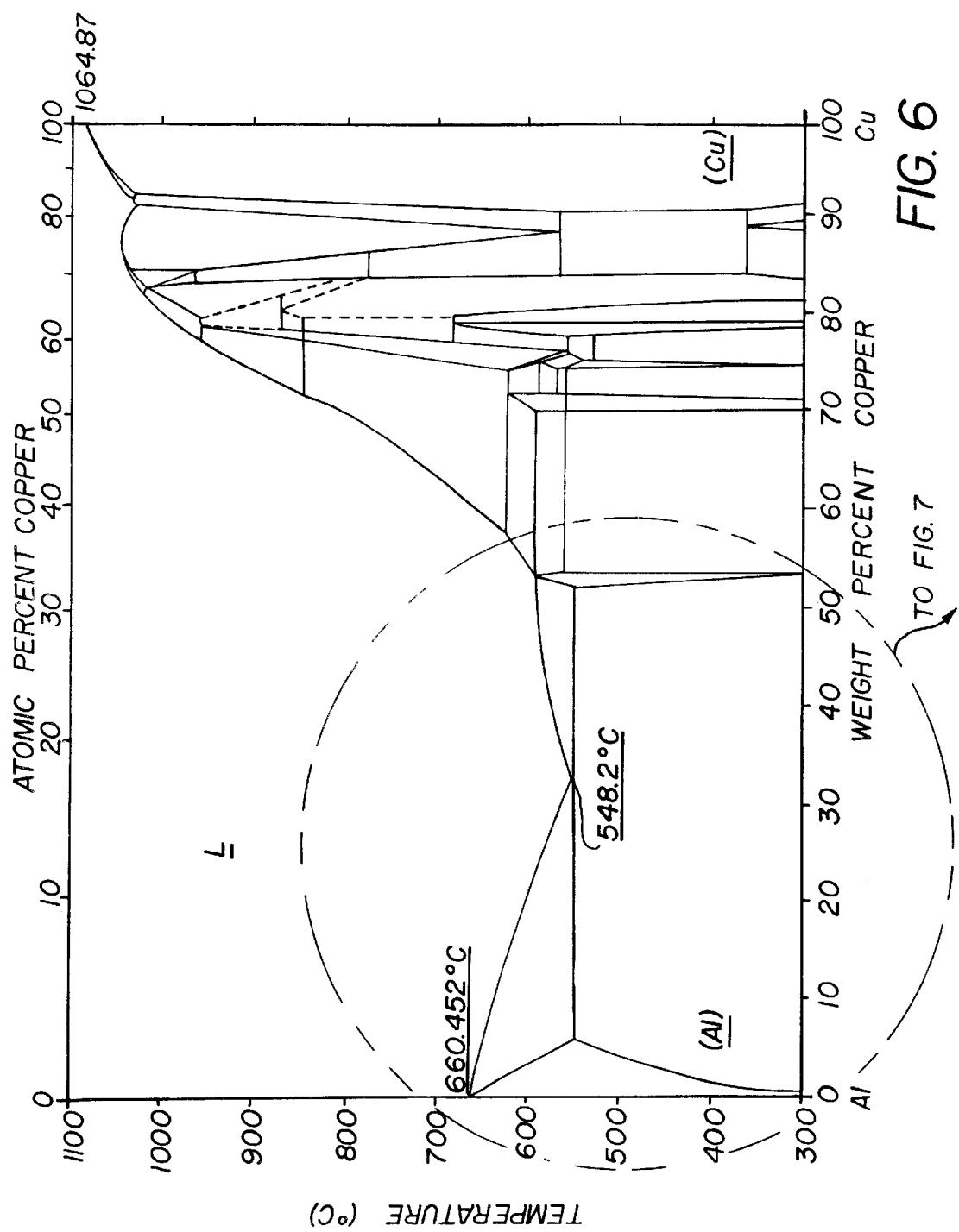

METHOD FOR OPTIMIZING MECHANICAL STRENGTH OF A CASTING USING MICROSTRUCTURE PREDICTIONS

TECHNICAL FIELD OF THE INVENTION

The present invention relates generally to aluminum castings, and, more particularly, to a method for predicting mechanical properties cast aluminum alloy structural components.

BACKGROUND OF THE INVENTION

Application of cast aluminum for engine structures has been increasing in recent years. These new applications include engine components for high power density and heavy duty service that were traditionally cast from gray iron. Individual aluminum alloy castings produced within a single production run can vary substantially in mechanical and physical properties. For example, tensile properties may vary between regions or locations in the same casting due to differences in local rates of solidification. Variations may also occur between castings due to slight changes within the acceptable limits for adding of the constituents to form the alloy and the latitudes of time and temperature of heat treatment and processing.

Historically, the tests conducted for determining the physical properties of a casting tended to destroy or weaken the casting. More recently, a testing method has been developed that is based on a relationship that correlates a microstructural parameter of a dendritic alloy sample to ductility. The method includes counting substantially all of the metal dendrite arms of the primary metal phase within a surface area of a selected location and correlating the number of metal dendrite arms per unit area to the ductility of the location. The number of dendrite arms is correlated to the ductility of the dendritic alloy by means of an equation:

$$EL = c\left(\frac{ANB - C}{D}\right),$$

where

EL=total average elongation (ductility) in percent,

N=number of cells of the primary metal of the alloy counted per unit area, and

A, B, C, D=empirical constants.

Further effort has refined the ductility equation to account for porosity of the sample. The method includes selecting a surface area of the casting for determining ductility; determining the number of metal cells of the primary metal within the surface area of the casting; measuring the aspect ratio of the eutectic particles and the porosity within the surface area of the casting; and determining ductility of the casting by relating the number of cells of primary metal per unit area with the measured aspect ratio of the eutectic particles and the measured porosity according to the equation:

$$EL = 10\left\{\frac{\left[C_1(N^{0.5}) - C_2\left(\frac{N^{0.5}}{AR}\right) + C_3\left(-\frac{1}{AR}\right) - C_4(P^{0.5}) - C_5 - c\right]}{(k+b)}\right\}$$

where

EL is the total average elongation (ductility of casting in percent),

N is the number of cells of the primary metal of the casting per unit area, $C_1(N^{0.5})$ is the solidification rate, $$C_1\left(\frac{N^{0.5}}{AR}\right)$$

is the solidification rate (SR), $$C_2\left(\frac{N^{0.5}}{AR}\right)$$

is the SR and eutectic modification (EM) interaction; AR is the aspect ratio of the eutectic particles, $$C_3\left(-\frac{1}{AR}\right)$$

is the EM from alloying and solution heat treatment, $C_4(P^{0.5})$ is the porosity, percent coverage, ductility reduction, $C_5$ is a coefficient characteristic of the chemistry of the alloy, and c, k, and b are empirical constants for the alloy and $C_1$, $C_2$, $C_3$, and $C_5$ are coefficients from statistical multiple regression of the alloy.

While progress has been made, designing components for high power density, heavy duty automotive applications reveals a lack of detailed information on the metallurgy of solidification of the aluminum alloys sufficient to predict mechanical and physical properties. It is desirable to predict physical and mechanical properties before a casting is made.

SUMMARY OF THE INVENTION

The present invention is directed to overcoming one or more of the problems set forth above. Briefly summarized, according to one aspect of the present invention, a method for quantitatively predicting and consequently minimizing the amount of certain critical phases (e.g. eutectic $Al_2Cu$) formed during solidification of Al—Si alloys used in a vehicle engine component or other structural component comprises developing a micromodel to simulate microstructure evolution in cast aluminum alloys, calibrating the micromodel using experimental thermal analysis cooling curves and an optimization process, simulating microstructure evolution and cooling curves in a casting using the calibrated micromodel, and predicting critical phase (e.g. $Al_2Cu$) precipitation in the casting as a function of solidification conditions.

The micromodel simulates microstructure evolution in castings such as 319 and A356 aluminum alloys which are similar in composition but differ in copper content. The model is calibrated using experimental thermal analysis cooling curves and an optimization methodology. The model is then used to simulate microstructure evolution and cooling curves in a special wedge casting. The model is able to predict critical phases (e.g. $Al_2Cu$) precipitation as a function of solidification conditions.

A basic finding for Al—Si—Cu alloys such as 319 Al is that at low cooling rates, a high degree of segregation of copper in liquid occurs which leads to a high amount of eutectic $Al_2Cu$. This condition leads to reduced strength due to depletion of Cu in the primary Al dendrite and low amount of fine θ″, θ′ and θ precipitates which form during heat treatment. At higher cooling rates the amount of copper available in liquid is less and a lower amount of eutectic Al$_2$Cu is formed. This leads to higher strength due to optimum levels of Cu in the primary Al dendrites and high amounts of the fine θ",θ' and θ precipitates which form during heat treatment. The model allows casting process variables to be varied with predictable results so that the casting process and resulting properties can be controlled via the micromodel.

This method can also be used to predict and control the influence of solidification conditions on formation of critical phases such as Al$_6$(Fe,Mn)$_3$Si and AlFe which result when present in Al—Si alloys.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 6 is an Al—Cu equilibrium phase diagram.

DETAILED DESCRIPTION OF THE PREFERRED EMBODIMENTS

Application of cast aluminum for engine structures has been steadily increasing in recent years. These new applications include engine components for high power density and heavy duty service that were traditionally cast from gray iron. Designing components for these applications has revealed a lack of detailed information on the metallurgy of solidification in these alloys.

A356 and 319 are two cast aluminum alloys used in powertrain structures such as the engine block and heads. Typical compositions in weight percent of these alloys is given in Table 1. the most significant difference between these two alloys is that A356 is predominantly an Al—Si alloy with less that 0.2% copper while 319 is mainly a Al—Si—Cu alloy with 3–4% Cu.

TABLE 1

| Element | A356 (%) | 319 (%) |
| --- | --- | --- |
| Si | 6.5–7.75 | 6.5–8.0 |
| Cu | 0.2 max | 3.0–4.0 |
| Mg | 0.25–0.06 | 0.2–0.5 |
| Mn | 0.1 max | 0.2–0.6 |
| Fe | 0.2 max | 0.8 max |
| Ni | 0.05 max | 0.3 max |
| Zn | 0.1 max | 0.8 max |
| Sn | 0.05 max | 0.1 max |
| Ti | 0.25 max | 0.25 max |
| Sr | 0.05 max | 0.05 max |
| Cr | 0.01 max | 0.01 max |

Typically, solidification of these alloys is described by a sequence of microstructure evolution including nucleation of primary aluminum phase, formation of a dendritic network of the primary aluminum phase, aluminum-silicon eutectic reaction, and precipitation of intermetallic phases (e.g. Al$_2$Cu and Al$_6$(Fe,Mn)$_3$Si).

Figure 1:
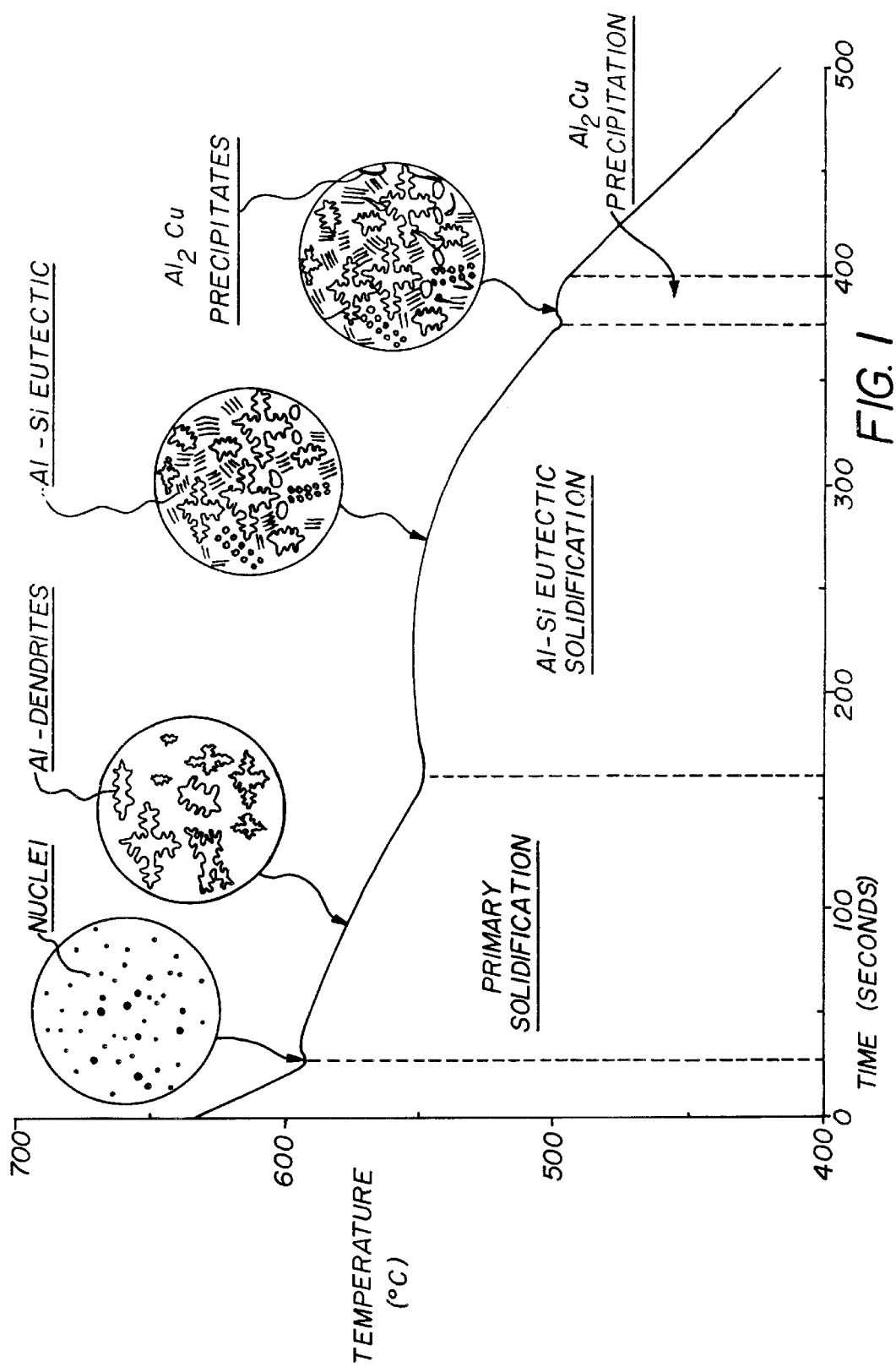
FIG. 1 is a schematic diagram illustrating various stages of microstructure evolution in 319 aluminum alloy corresponding to different regions of a thermal analysis cooling curve.

A schematic of microstructure evolution corresponding to various stages of solidification in a thermal analysis cup is shown in FIG. 1. The evolved microstructure controls the mechanical properties of the alloy which determines the performance of these cast components in service.

Most castings have a variety of microstructures that result from the range of solidification times observed between thick and thin sections of the casting. Cylinder blocks and heads are no exception. Characterization of mechanical and physical properties is normally accomplished by machining test bars from sections cut from these castings.

Figure 2:
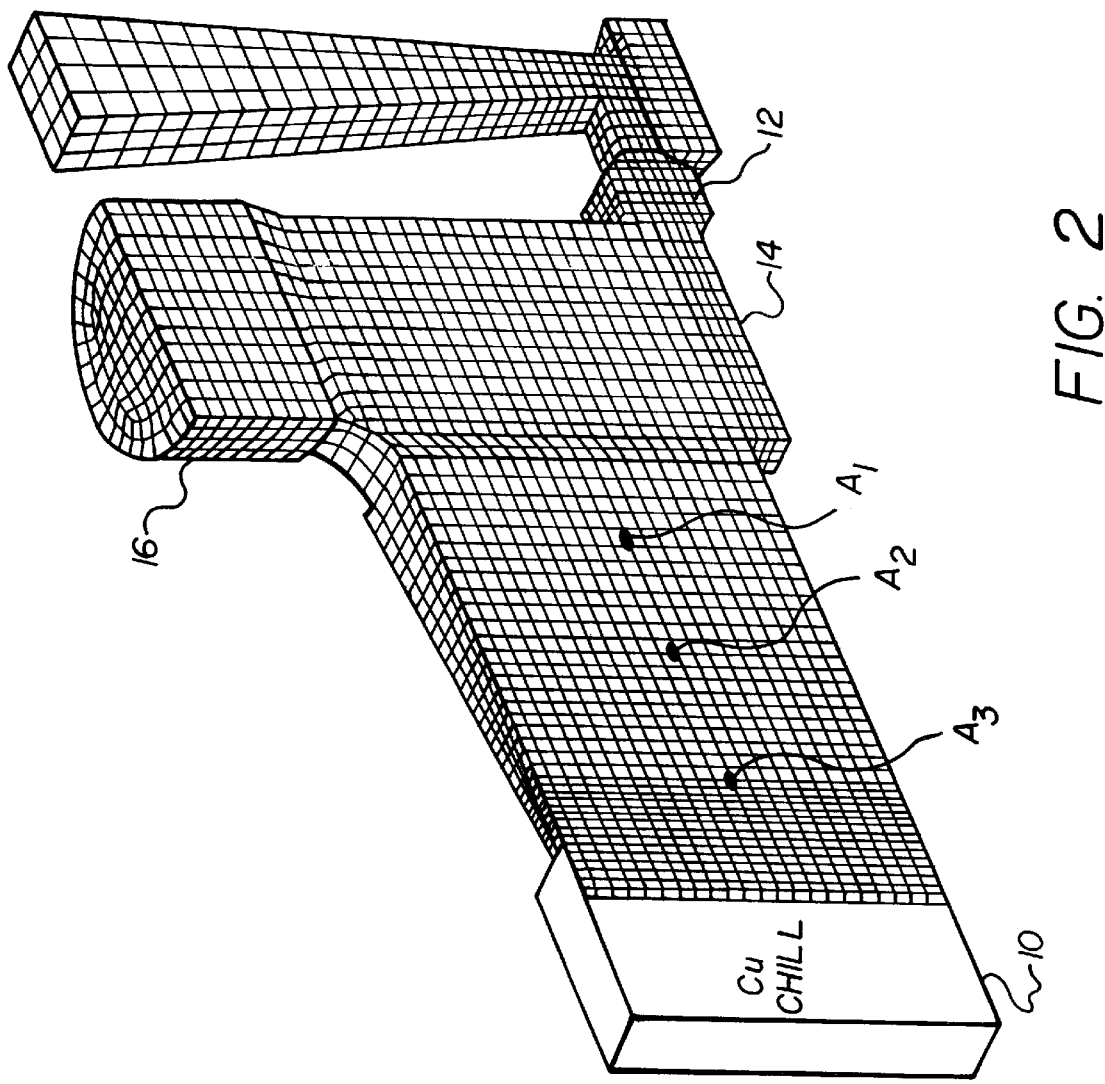
FIG. 2 is a schematic diagram of a wedge casting.

In cylinder blocks and heads, it is not possible to obtain test samples from critical regions of the casting due to shape and thickness constraints. It is also difficult to conduct systematic studies of alloy and heat treatment effects on components for the same reasons. Therefore, a need exists to design a casting from which test samples with uniform microstructures could be machined, and to produce samples that cover the range of microstructures observed in production components. To accomplish this task, a wedge design was chosen (FIG. 2). The mold for the wedge casting was made from resin bonded silica sand with a copper block 10 placed at the thin end of the wedge to serve as a chill. The chill creates parallel isotherms in the casting progressing from the thin end to the thick due to relatively high thermal conductivity and specific heat of copper. Ceramic foam filters 12 were placed in the runner 14 to control flow and remove inclusions. The wedge was cast vertically in order to ensure even filling of the mold. A large riser 16 was located at the thick end of the wedge to feed the casting and to ensure long solidification times.

The material for these experiments was purchased in the form of pre-alloyed ingots. The alloy was melted in a gas furnace with a charge consisting of both ingots and returns (risers) from previous castings made from the same lot of material. After the charge was completely molten, degassing was effected using a $N_2$—5% $SF_6$ gas mixture through a rotary degasser. After degassing, the hydrogen concentration of the melt was evaluated using a reduced pressure test sample and by the gas recirculation technique.

Modification of the eutectic silicon was effected by addition of Al—10% Sr master alloy in the form of either waffle ingots or cut rod. The master alloy was added immediately after the degassing operation. The target Sr level was 200 ppm. Approximately twenty minutes after the master alloy addition, the castings were poured. Solidification times ranged from approximately 15 second near the chill to 2300 seconds in the riser. The wedges were allowed to solidify in the sand molds followed by shake-out.

For tensile specimens the wedge was first machined to obtained rectangular bars. These rectangular sections underwent a simulated thermal sand removal (TSR) heat-treatment of 1 hour, at 495° C. followed by an air cool to room temperature. Then each bar was given a T6-type heat treatment consisting of 8 hours at 495° C. followed by a boiling water quench and aging for 5 hours at 190° C. The heat treatment was conducted batch-style in electrical-resistance air-circulated furnaces. Thermocouples were attached to samples and the temperature was controlled to ±5° C. including overshoot during heat-up to temperature. The boiling water quench was monitored to ensure that the temperature was between 90° C. and 96° C.; samples were kept in the boiling water quench for a minimum of 5 minutes. A maximum time interval of 15 minutes existed between removal from the quench and placing the samples in the aging furnace.

Samples for tensile test were subsequently machined from each of the rectangular bars. The tests were conducted on a hydraulically-actuated MTS 810 frame equipped with a 458 microprocessor controller. Prior to testing, a precision alignment device was used to minimize frame bending strains to less than 40 $\mu\epsilon$. The tensile tests were performed in stroke control with an initial strain rate of $2.167 \times 10^{-2}$ mm/mm.sec. A minimum of 4 specimens in each region of the wedge were tested at room temperature in laboratory air.

Figure 3:
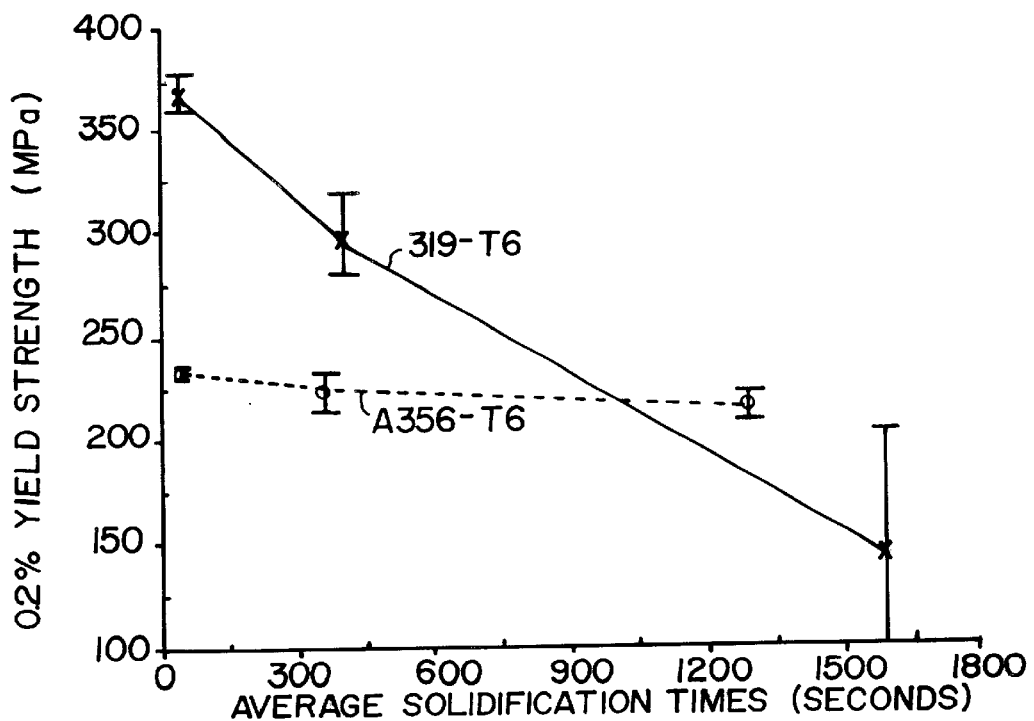
FIG. 3 is a graph showing the influence of solidification time on yield strength of 319 and A356 aluminum alloy in a heat treat condition.

FIG. 3 details the effect of solidification time on the tensile yield strength (TYS) of the 319-T6 and the A356-T6 alloys. As FIG. 3 shows, the TYS of the A356-T6 is constant while that of 319-T6 varies significantly with solidification time. The lower solidification times correspond to regions near the chill while the higher solidification times correspond to the thicker regions of the wedge away from the chill.

Figure 4:
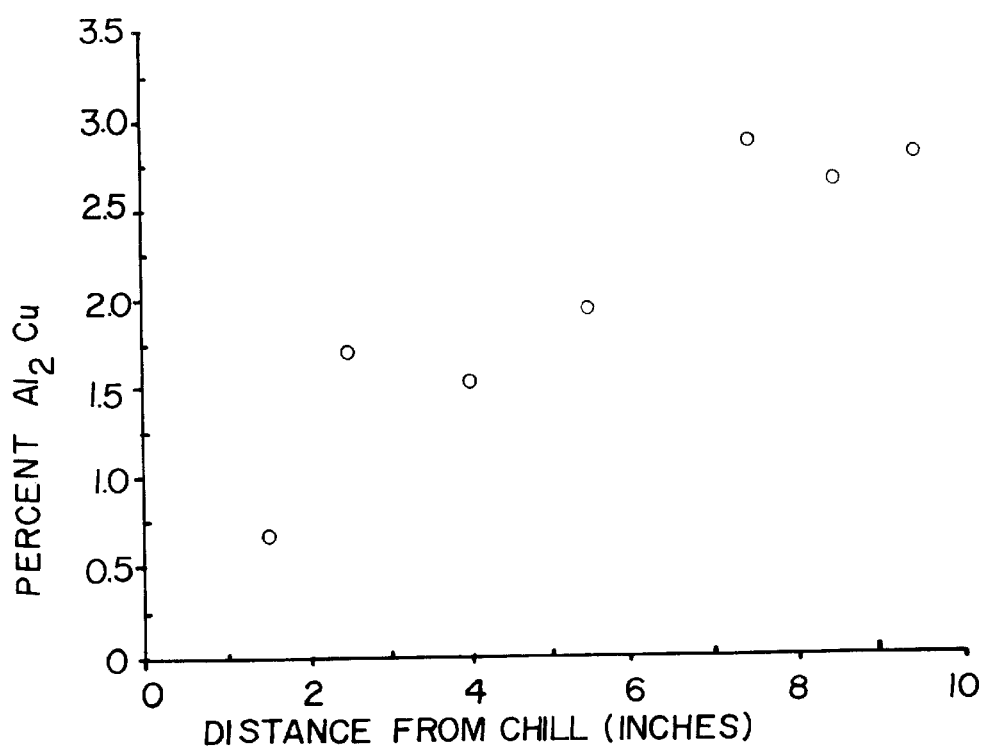
FIG. 4 is a graph illustrating observed area fraction of eutectic Al$_2$Cu versus location in a 319 wedge casting.

Samples for quantitative metallography were cut from the wedge at eight locations, (0, 1.5, 2.5, 4.0, 5.5, 7.5, 8.5 and 9.5 inches from the chill). The samples were polished and analyzed for area fraction $Al_2Cu$. FIG. 4 shows a plot of the obtained area fraction $Al_2Cu$ as a function of distance from the chill. As seen in FIG. 4, greater amounts of $Al_2Cu$ were found in slower cooling sections. Because these sections also had lower TYS, it is believed that volume fraction of eutectic $Al_2Cu$ influenced TYS. This belief is supported by the fact that A356, which has very little Cu (<0.2%) had more uniform TYS between the thicker and thinner sections of the wedge. This is consistent with the concept that yield strength of Al—Si—Cu alloys is expected to increase with increasing amounts of dissolved copper, which produces higher volume fractions of the fine θ' ($Al_2Cu$) strengthening precipitates.

Equations have been developed to represent the growth kinetics of various phases as a function of undercooling. Solute redistribution models have been developed to track local concentrations of Si and Cu as solidification proceeds.

One requirement for kinetics and solute redistribution models is the Al—Si—Cu ternary phase diagram. Because limited information is available on the Al—Si—Cu ternary and Al-rich multicomponent phase diagrams, several assumptions and approximations have been made to calculate phase transformation temperatures and partition coefficients. The precision of these models would be substantially improved by application of a thermodynamic phase diagram calculation program such as THERMOCALC.

Figure 5:
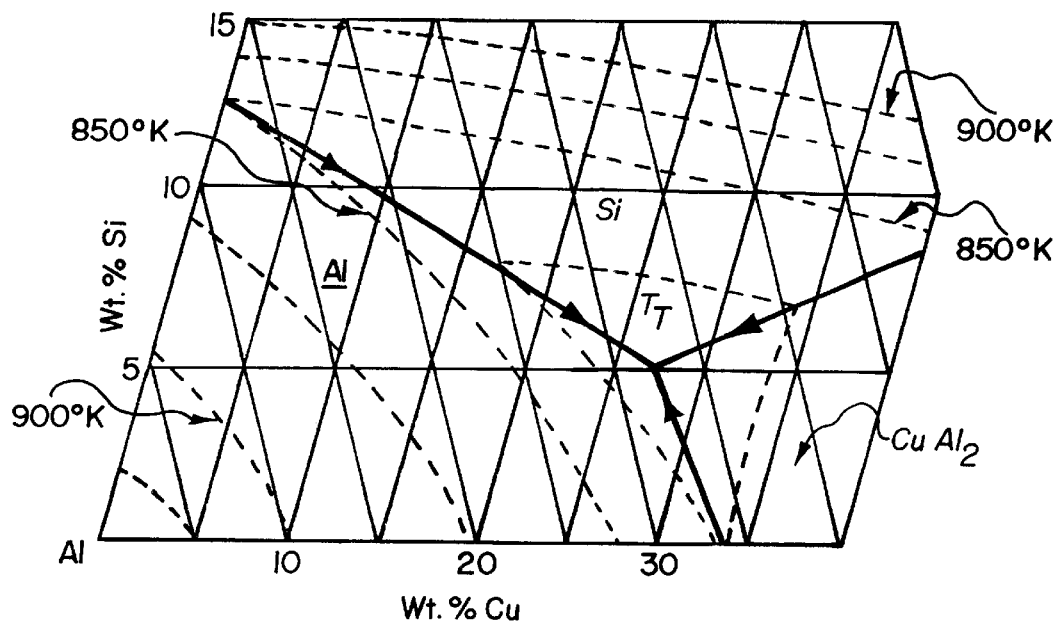
FIG. 5 is a region of an Al—Si—Cu phase diagram.

The Al-rich corner of the Al—Si—Cu phase diagram shown in FIG. 5 is used to obtain approximations for the aluminum liquidus ($T_{AlL}$) and Al—Si eutectic temperatures ($T_{AlSiE}$):

$$T_{AlL}=664-7.2(\% \text{ Si})02.9(\% \text{ Cu}) \qquad (1)$$

$$T_{AlSiE}=577.8-1.6(\% \text{ Cu})$$

The Al—Si eutectic temperature is the intersection of the aluminum and silicon liquidus in FIG. 5. The liquidus temperatures have been approximated by a plane and the eutectic temperature, to a line. Because FIG. 5 represents only a selected region of the Al—Si—Cu phase diagram (i.e. Cu≦40%, Si≦15%), it cannot be used to obtain the $Al_2Cu$ liquidus and the ternary eutectic temperature $T_T$. Experimental thermal analysis cooling curves are used to locate the thermal arrest corresponding to $Al_2Cu$ precipitation and this temperature (=505° C.) is used as the ternary eutectic temperature.

Information about coefficients for partition of Cu and Si between aluminum and the liquid ($k_{cu}$, $k_{si}$) are not readily available, therefore binary partition coefficients have been used. For $k_{si}$ a constant value of 0.13 was used while for $k_{cu}$ a temperature dependent polynomial expression was obtained from published literature.

$$K_{cu}=1.1317138(10)^4-66.910962T+0.15815355T^2-1.8679168(10)^{-4}T^3+1.1023244(10)^{-7}T^4-2.6001967(10)^{-11}T^5. \qquad (2)$$

Figure 7:
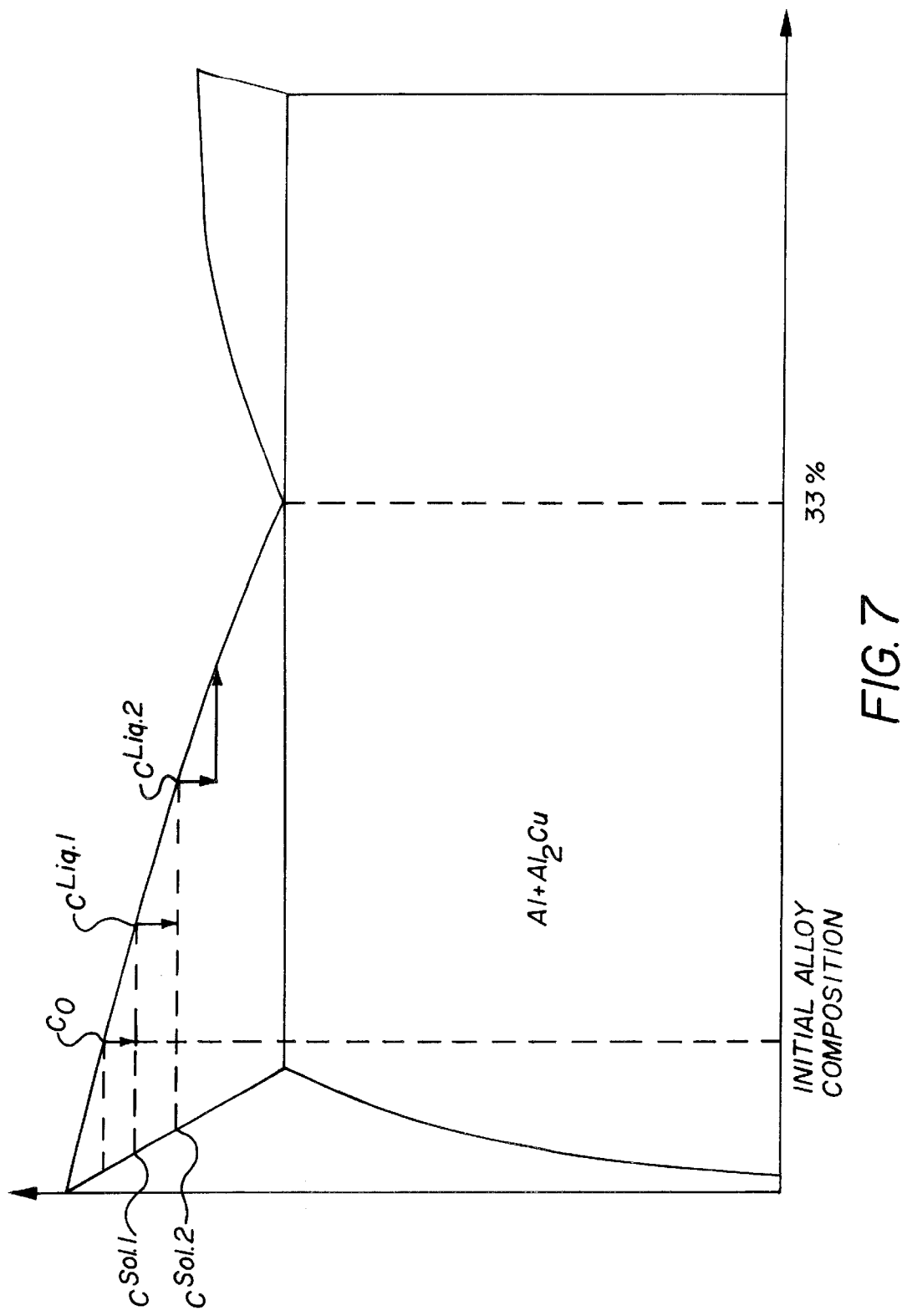
FIG. 7 is a somewhat enlarged portion of the phase diagram of FIG. 6.

Referring to FIGS. 6 and 7, to illustrate the role of the partition coefficient during solidification, when an alloy of composition $C_0$ is cooled below the liquidus (i.e. undercooled), it precipitates out solid with composition $C^{sol,1}$ and the remaining liquid changes in its composition $C^{liq,1}$. On further cooling the liquid, now of composition $C^{liq,1}$ transforms to a liquid of composition $C^{liq,2}$ while precipitating out a solid of composition $C^{sol,2}$ and so on. The ratio of solute in the solid to that in the liquid is actually the ratio of the slopes of the solidus to liquidus. This ratio is known as the partition coefficient, k. The lower the partition coefficient, the greater the solute enrichment of the liquid.

An important point to note is that the slope of the solidus and the liquidus is not a constant. The solidus and liquidus become more parallel as the temperature decreases. Thus, the partition coefficient increases. A higher partition coefficient indicates less solute being rejected into liquid.

With no convection transport of liquid or solid, heat transfer for the solidification problem is described by, $$\nabla(k\nabla T) + g = \rho c \frac{\partial T}{\partial t} \quad (3)$$

where c is the specific heat and g is the rate of latent heat generation given by, $$g = \rho L \frac{dV_s}{dt}, \quad (4)$$

where $\rho$ is the density, L is the latent heat of solidification and $V_s$ is the instantaneous volume fraction solid. Micromodeling involves the prediction of the rate of latent heat generation (g) and fraction solid evolution consistent with observed cooling behavior of the alloy, fraction of phases in the solid, and solute redistribution and local composition during the course of solidification.

For the finite element model, these quantities are computed at each node. A generalized model for microstructure evolution during solidification is described in the following paragraphs.

Typical models for growth of equiaxed dendritic and eutectic grains are represented as parabolic functions of undercooling $$\frac{dR_i}{dt} = \mu_i(\Delta T)^2, \quad (5)$$

where $R_i$ is the radius of the grain, $\mu i$ is the growth kinetics coefficient of phase i and $\Delta T$ is the undercooling with respect to the equilibrium transformation temperature. Assuming the grains to be of uniform size and approximating them with equivalent spheres, the volume fraction of a phase i can be obtained using the grain radius $$V = n(t)\frac{4\pi R_i^3}{3} \quad (6)$$

The rate of evolution of phase i is given by $$\frac{dV_i}{dt} = n(t)4\pi R_i^2 \frac{dR_i}{dt}\Psi(V_S) \quad (7)$$

n(t) is typically evaluated using a nucleation model. Reliable nucleation models are not easily available for these foundry alloys, so a constant time independent number of grains, n, are assumed to be growing during the course of solidification. A cooling rate dependent equation obtained using ProCAST database is used to estimate the constant grain density (n):

$$n = 1667.8 + \left(291.6\frac{dT}{dt}\right) / cm^3 \quad (8)$$

From equations 5, 6 and 7

$$\frac{dV_i}{dt} = K_i(V_i)^{\frac{2}{3}}(n)^{\frac{1}{3}}\Delta T_i^2(\Psi(V_s)), \quad (9)$$

where $K=(4\pi)^{1/3}(3)^{2/3}\mu_i$,
and $\Psi=(1-V_s)^a$.

ProCAST is a commercially available program from Universal Energy Systems, Dayton, Ohio.

The kinetics model in Equation 9 is used for representing both primary and eutectic growth. In the case of solidification of primary phase ($T<T_{AlL}$)

$$\frac{dV_p}{dt} = K_p(V_p)^{\frac{2}{3}}(n_p)^{\frac{1}{3}}\Delta T_p^2(1-V_s)^a \quad T < T_{AlL} \quad (10)$$

where $K_p=(4\pi)^{1/3}(3)^{2/3}\mu_p$, and $\Delta T_p=T_{AlL}-T$.
For the growth of the Al—Si eutectic ($T<T_{AlSiE}$)

$$\frac{dV_e}{dt} = K_e(V_e)^{\frac{2}{3}}(n_e)^{\frac{1}{3}}\Delta T_e^2(1-V_s)^a \quad T, T_{AlSiE} \quad (11)$$

where $K_e=(4\pi)^{1/3}(3)^{2/3}\mu_e$, and $\Delta T_e=T_{AlSiE}-T$.
A Scheil type equation is used to estimate microsegregation of alloying elements $$\frac{dc_{Si}^l}{dt} = \frac{c_{Si}^l(1-k_{Si})}{f_l}\frac{df_s}{dt}, \quad (12)$$

$$\frac{dc_{Cu}^l}{dt} = \frac{c_{Cu}^l(1-k_{Cu})}{f_l}\frac{df_s}{dt}, \quad (13)$$

where $c_i^l$ is the concentration of element i in liquid and $k_i$ represents the equilibrium partition coefficient of element i. The Scheil equation is widely used to model microsegregation in alloys. An assumption of the equation is that there is no back diffusion in solid while the liquid is completely mixed.

Once the temperature falls below the Al—Si—$Al_2$ eutectic, $Al_2Cu$ precipitation begins. The rate of growth of the ternary eutectic is given by:

$$\frac{dV_c}{dt} = K_c(V_c)^{\frac{2}{3}}(n_c)^{\frac{1}{3}}\Delta T_c^2\left(\frac{f_c^{max}-f_c}{f_c^{max}}\right), \quad T < T_{AlSiE} \quad (14)$$

where $K_{ec}=(4\pi)^{1/3}(3)^{2/3}\mu_c$, $\Delta T_C=T_{AlCuE}-T$, and $f_c$ is the mass fraction of the eutectic. It is assumed that $n_c=n_e=n_p=n$. $f_c^{max}$ gives the maximum mas fraction of the eutectic that can be formed and is limited by the amount of copper dissolved in the liquid at the start of this eutectic reaction $$f_l c_{Cu}^l = f_c^{max} c_{Cu}^e \quad (15)$$

where $c_{Cu}^e$ is the eutectic composition (=33 wt. % based on the binary Al—Cu phase diagram). From the mass fraction of eutectic the actual mass fraction of $Al_2Cu$ is calculated using a lever rule and then converted to a volume fraction. It should be noted that there is an inconsistency here. The mass balance is done using a binary Al—Cu phase diagram (FIGS. 6–7) but the eutectic transformation temperature is obtained from thermal analysis data for actual multicomponent 319 alloy. The desire here is to develop a methodology which can be used for quantitative predictions once the necessary thermodynamics and phase diagram information for the system have been developed.

The basis of the Al$_2$Cu prediction is that at slower cooling rates the segregation of Cu in liquid is greater and hence more Cu is available for precipitation once the ternary eutectic temperature is reached. For example the following simple example shows basic calculations involved in evaluating the maximum volume fraction of Al$_2$Cu that can be formed. For a given alloy and solidification rate, if we assume that the mass fraction of liquid is 10% and the amount of copper in the liquid is 25%, then, when the temperature goes below the Al$_2$Cu eutectic (505° C.), the maximum mass fraction of the Al—Al$_2$Cu eutectic that can be formed using equation 15 is given by $$(10)(25) = f_c^{max}(33) \tag{16}$$

$$f_c^{max} = 7.58\%.$$

For this alloy and solidification rate a maximum of 7.58% mass fraction of the eutectic can be formed with this amount of copper. Using the lever rule for binary Al—Al$_2$Cu eutectic (FIGS. 6–7), the maximum mass fraction of Al$_2$Cu that can be formed in the eutectic is $$f_{Al_2Cu}^{max} = 4.4\%. \tag{17}$$

Since Al$_2$Cu (4.0 g/cm$^3$) is denser than Al converting this to a volume fraction gives $$V_{Al_2Cu}^{max} = 3.0\% \tag{18}$$

A point to note here is that the maximum amount of Al$_2$Cu that can precipitate is both a function of the copper concentration in liquid and the total fraction-of-liquid at the ternary eutectic temperature. Also, since the kinetics model is dependent on undercooling, different cooling rates produce different fraction solid curves. At higher cooling rates, the copper concentration in liquid is lower due to lower microsegregation while the fraction liquid might be relatively high. Therefore, in this model, if the influence of the fraction of liquid dominates, it is possible to obtain higher amounts of Al$_2$Cu at higher cooling rates though, it is generally not the case. Electron microprobe work is consistent with the trend of increasing eutectic Al$_2$Cu precipitation with decreasing cooling rate, because it indicates greater concentration gradients across dendrite arms for slower cooling sections as opposed to faster cooling sections. This implies greater segregation of copper in slower cooling sections. Thus, $f_c^{max}$ in equation 14 is a function of solidification rate and it varies from position to position in the wedge.

Figure 8:
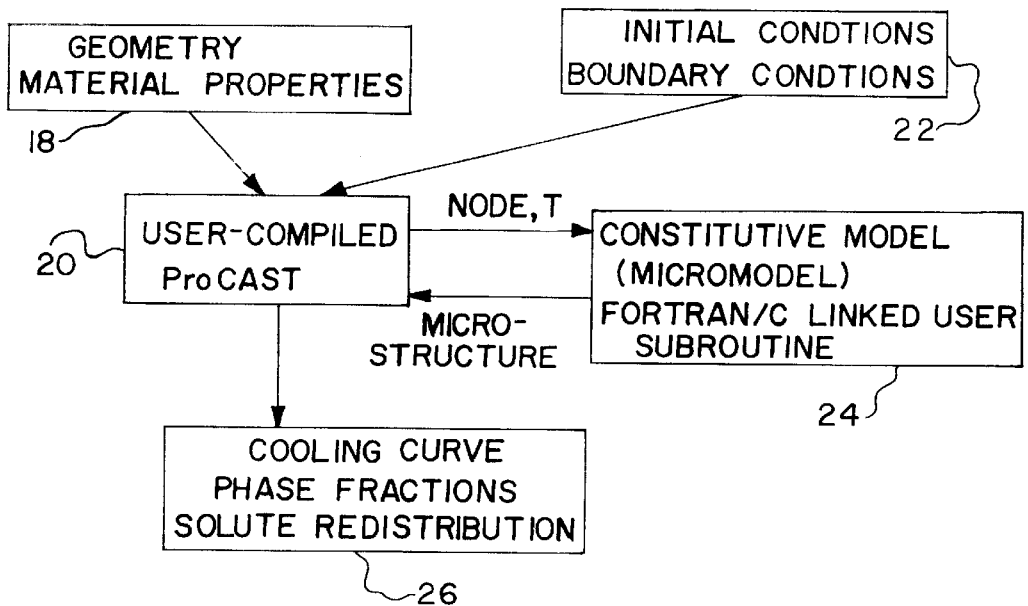
FIG. 8 is a block diagram illustrating implementation of the micromodel in ProCAST which is a casting simulation program.

FIG. 8 shows overall implementation architecture of the micromodel in ProCAST. In FIG. 8, block 18 represents geometric and material properties that are input to block 20, the user-compiled ProCAST. Block 22 represents initial conditions and boundary conditions that are also input to block 20. Block 24 is the micromodel with a Fortran/C linked user subroutine. Block 26 represents the cooling curves, phase fractions and solute redistribution.

ProCAST provides a set of libraries (in an object file) called prolib.o. It also provides a template for a user routine which is called user-micro.c. The data structures used in the routine are located in common.h. The micromodel developed in this work is a FORTRAN subroutine called micro319.f and this routine is called from within user-micro.c. The three pieces (prolib.o, user-micro.c and micro319.f) are complied and linked together (in a "makefile") to create a customized version of ProCAST called Procast-319. Procast-319 is used in the same manner as ProCAST.

Figure 9:
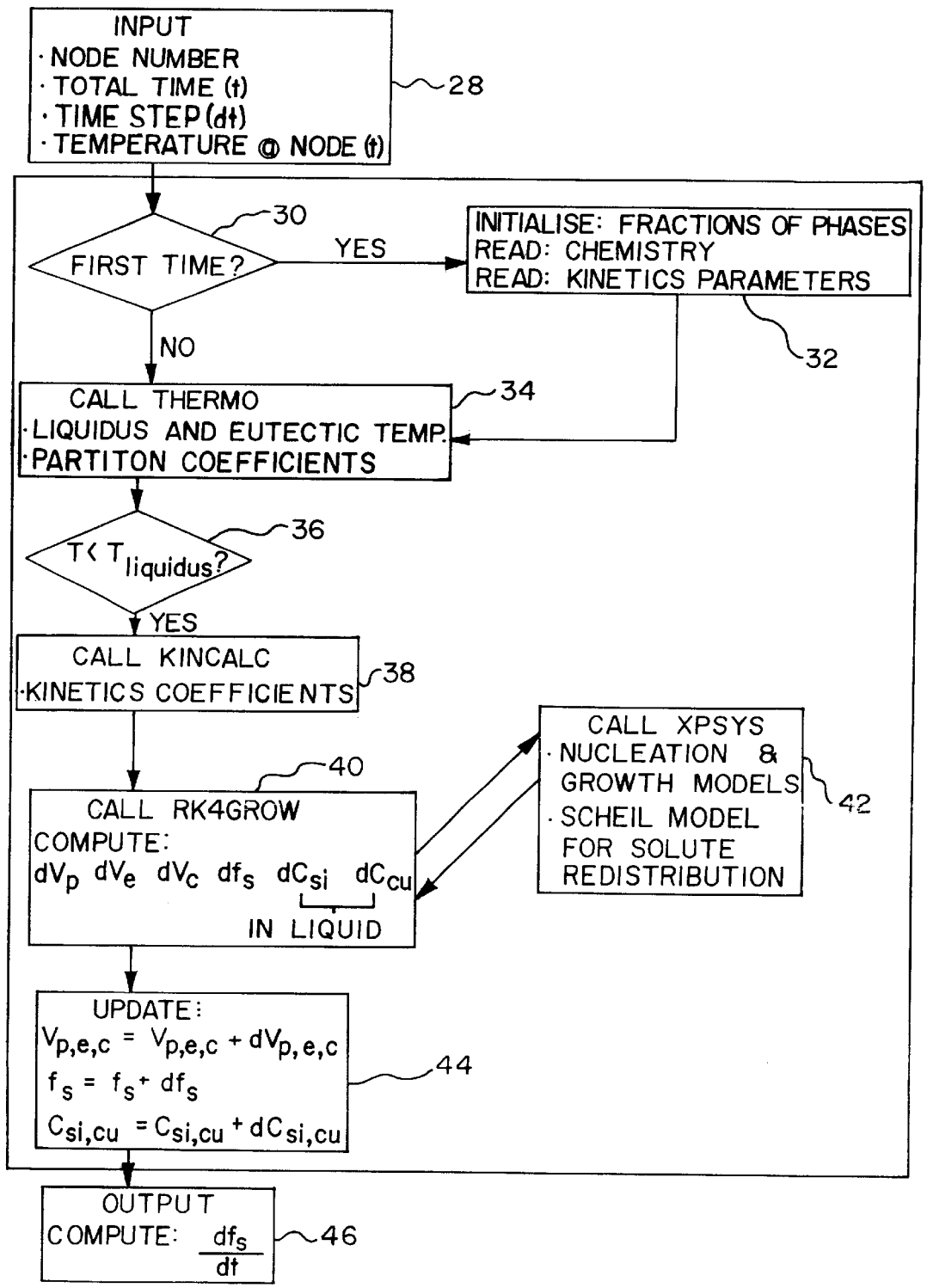
FIG. 9 is a flow chart illustrating a micromodel FORTRAN subroutine called micro319.f.

FIG. 9 is a flow chart illustrating the architecture of micro319.f wherein input block 28 receives data from ProCAST solution in the form of node numbers, total time, time step and temperature. At decision block 30 it is decided if this is the first time through. If so, the phase fractions are initialized and the chemical and kinetic parameters are read at block 32 before progressing to block 34. If not, the system progresses directly to block 34 where subroutine THERMO which provides the liquidus and eutectic temperatures for calculating partition coefficients. When the temperature is below the liquidus temperature at block 36, subroutine KINCALC calculates kinetics coefficients at block 38 after which subroutine RK4GROW is used at block 40 to solve system of initial value problems. At block 42 subroutine XPSYS provides experimental data. The values computed at block 40 are updated at block 44 and the rate of change of the mass fraction is calculated at block 46 and returned to the main program.

Figure 10:
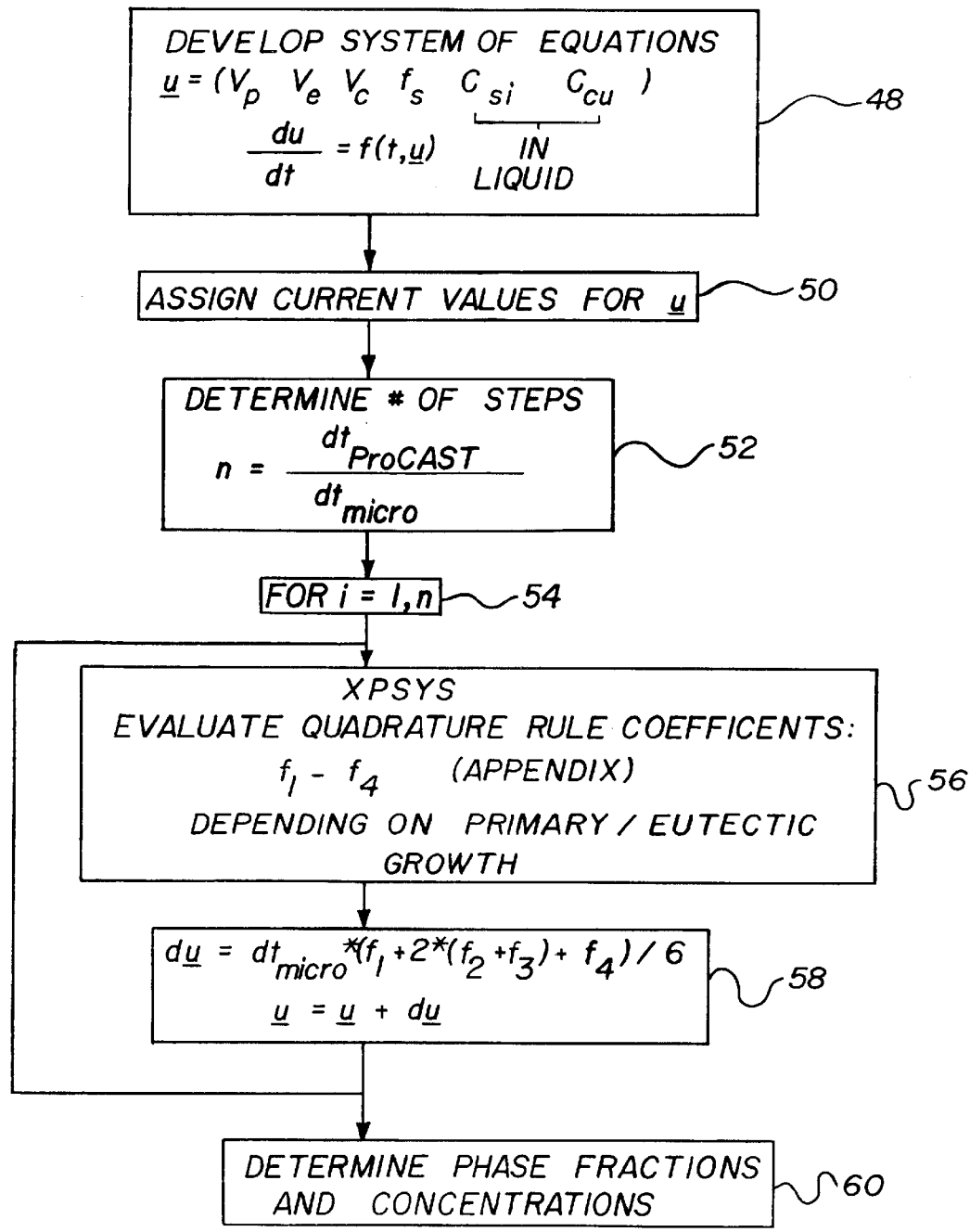
FIG. 10 is illustrating architecture of a subroutine called RK4GROW.

FIG. 10 further illustrates subroutine RK4GROW where the system of equations is developed in block 48 with current values assigned at block 50. Block 52 determines the number of time steps, one of which is selected at block 54. At block 56 subroutine XPSYS is called on to evaluate quadrature rule coefficients that are used for the solution at block 58. At block 60 the phase fractions and concentrations are determined.

The RK4GROW module consists of a 4$^{th}$ order Runge-Kutta solution scheme used to solve the system of initial value problems that are described by Equations 7–14. These initial value problems are a set of ordinary differential equations.

The fourth order classical Runge-Kutta for the system of equations $$\frac{du}{dt} = f(t, u) \tag{19}$$

$$u(t_0) = \eta$$

may be written as $$u_{j+1} = u_j + \frac{1}{6}(K_1 + 2K_2 + 2k_3 + K_4) \tag{20}$$

where $$K_1 = \begin{matrix} K_{11} \\ K_{21} \\ \vdots \\ k_{n1} \end{matrix}, K_2 = \begin{matrix} K_{12} \\ K_{22} \\ \vdots \\ k_{n2} \end{matrix}, K_3 = \begin{matrix} K_{13} \\ K_{23} \\ \vdots \\ k_{n3} \end{matrix}, K_4 = \begin{matrix} K_{14} \\ K_{24} \\ \vdots \\ k_{n4} \end{matrix}, \tag{21}$$

and $$K_{i1} = hf_i(t_j, u_{1,j}, u_{2,j} \ldots, u_{n,j}) \tag{22}$$

$$K_{i2} = hf_i(t_j + h/2, u_{1,j} + \tfrac{1}{2}K_{11, u2,j} + \tfrac{1}{2}K_{21}, \ldots, u_{n,j} + \tfrac{1}{2}K_{n1})$$

$$K_{i3} = hf_i(t_j + h/2, u_{1,j} + \tfrac{1}{2}K_{12, u2,j} + \tfrac{1}{2}K_{22}, \ldots, u_{n,j} + \tfrac{1}{2}K_{n2})$$

$$K_{i4} = hf_i(t_j + h, u_{1,j} + K_{13, u2,j} + K_{23}, \ldots, u_{n,j} + K_{n3}),$$

i=1,n

The equation solves for $u_{j+1}$, once $u_j$ are known. The coefficients K's are the quadrature rule coefficients. The initial value (at t=0) for each of the variables, is taken to be the current value at the beginning of a time step. The time domain is the overall time step (ProCAST solution) and sub-incrementing is employed to step through the time step. The equations therefore are solved for the variables an the left hand side of Equations 7–14 at the end of each time step. FIG. 10 shows the structure of RK4GROW. THERMO is a subroutine which returns the liquidus and eutectic temperatures for the instantaneous local composition of the solidifying liquid. This subroutine contains approximations of the aluminum liquidus and the silicon liquidus. KINCALC returns $K_p$, $K_e$ and $K_c$. Subroutine KCALC returns the partition coefficient of copper as a function of temperature.

A number of points must be kept in mind while implementing a micromodel in ProCAST: The flag MICRO in the p.dat file must be set to 2. The last line in the p.dat file should be USER 2.

The micromodel option in PreCAST should be activated for the solidifying material. This option can be found under material properties. Other than the user-defined micromodel, ProCAST has its own set of micromodels for dendritic and eutectic solidification. Because the micromodel option has been activated, ProCAST expects the user to select one of these micromodels in PreCAST. To make sure that the selected ProCAST micromodel does not interfere with the actual user-defined micromodel (user-micro.c+micro319.f) the transformation temperature for activation of the ProCAST micromodel is set to a very low value (−270° C.). This assures that the ProCAST micromodel selected is never called.

The micromodel variables ($V_p$, $V_e$, $V_c$, $c_{Si}^1$ and $c_{Cu}^1$) are stored in arrays during the run. Each element of an array corresponds to a node. Since, ProCAST enters the module multiple times in the same time-step until convergence is achieved, care must be taken to make sure that the arrays do not get updates more than once for the same time-step. Only the final converged value should be used for updating the array for every time-step.

Node reassignment takes place within the user-defined subroutine. Thus, the ProCAST node number must not be confused with the node number in the user-defined subroutine. The micromodel uses only the nodes in the casting part of the model.

Optin and micin are the two input files for the micromodel. Optin consists of the optimized micromodel kinetics parameters used for micromodel simulations while micin contains melt temperature and chemistry and the node numbers for nodes of interest. Contents of input file micin are shown below in Table 2.

TABLE 2

| | |
|---|---|
| 650.0° C.: | Initial melt temperature (t_pour) |
| 3.5%: | Initial concentration of copper in the melt in weight % (c_o_cu) |
| 7.5%: | Initial concentration of silicon in the melt in weight % (c_o_si) |
| 331: | ProCAST node number for the 9 inch section of the wedge (i_node_out_1) |
| 335: | ProCAST node number for the 6 inch section of the wedge (i_node_out_2) |
| 341: | PrOCAST node number for the 2 inch section of the wedge (i_node_out_3) |
| 333: | PrOCAST node number for another node of interest (i_node_out_4) |
| 338: | PrOCAST node number for another node of interest (i_node_out_5) |

The ViewCAST menu has provisions under the micromodel option, to plot micromodel parameters such as dendrite radius, dendrite tip composition etc. For the purpose of plotting $Al_2Cu$ precipitation, the program user-micro.c has been modified such that the array assigned for storing the nodal dendrite radius information actually contains the volume fraction of $Al_2Cu$ for the node. On selecting dendrite radius in the ViewCAST menu plot for $Al_2Cu$ precipitation can be obtained. A point to note is that ViewCAST reads the file prefixm.2unf while user-micro.c writes to the file prefixum.unf. Thus, after the run is complete prefixmu.unf has to be copied to prefixm2.unf.

Once the model is formulated and implemented, it is then calibrated using an optimization technique. The calibration methodology uses the optimization tool OPTCAST (coupling DOT and ProCAST).

Figure 11:
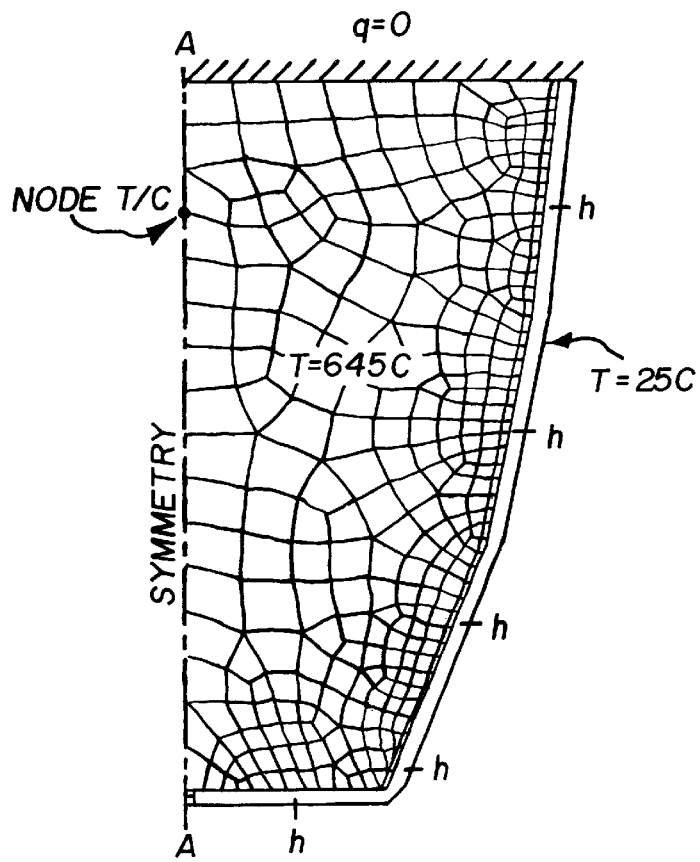
FIG. 11 illustrates a finite element mesh for a thermal analysis cup showing boundary conditions and initial conditions.

Cooling curves obtained from thermal analysis cups are used for the optimization. The finite element cup model used is shown in FIG. 11. The model consists of 395 4-noded quadrilateral elements and 502 nodes. The model is axi-symmetric about axis AA. Node T/C shows the location where the experimental and stimulated cooling curves are compared. A convection boundary condition is applied at the aluminum-steel cup interface and at the steel-air interface. The heat transfer coefficients are determined by optimization as described below. Tables 3–11 give optimized heat transfer coefficients (HTC) for the ProCAST models of the cup and the wedge.

TABLE 3

| T (° C.) | HTC (W/m² .K) |
|---|---|
| 25 | 100.0 |
| 400 | 173.5 |
| 600 | 398.2 |
| 615 | 3000.0 |
| 750 | 3000.0 |

Table 3 presents optimized interface heat transfer coefficients between Aluminum and Steel in the 319 cup model.

TABLE 4

| T (° C.) | HTC (W/m².K) |
|---|---|
| 0 | 725.6 |
| 500 | 900.0 |
| 2000 | 900.0 |

Table 4 presents optimized heat transfer coefficients for the aluminum/sand and copper/sand interfaces for 319 2D-wedge model.

TABLE 5

| T (° C.) | HTC (W/m².K) |
|---|---|
| 1 | 500.0 |
| 200 | 491.4 |
| 400 | 3454.4 |
| 570 | 5248.9 |
| 614 | 3270.2 |
| 700 | 5019.4 |
| 2000 | 5019.4 |

Table 5 presents optimized heat transfer coefficients for the aluminum/copper interface for 319 2D-wedge model.

TABLE 6

| T (° C.) | HTC (W/m².K) |
|---|---|
| 25 | 99.0 |
| 400 | 169.2 |
| 600 | 382.6 |
| 615 | 3000.0 |
| 750 | 3000.0 |

Table 6 presents optimized interface heat transfer coefficients between Aluminum and Steel in the A356 cup model.

TABLE 7

| T (° C.) | HTC (W/m².K) |
|---|---|
| 0 | 282.0 |
| 500 | 435.4 |
| 2000 | 435.4 |

Table 7 presents optimized heat transfer coefficient for the aluminum/sand and copper/sand interfaces for A356 2D-wedge model.

TABLE 8

| T (° C.) | HTC (W/m².K) |
|---|---|
| 1 | 500.0 |
| 200 | 343.7 |
| 400 | 3085.3 |
| 570 | 5148.0 |
| 614 | 3265.9 |
| 700 | 4894.8 |
| 2000 | 4894.8 |

Table 8 presents optimized heat transfer coefficient for the aluminum/copper interface for A356 2D-wedge model.

TABLE 9

| T (° C.) | HTC (W/m².K) |
|---|---|
| 0 | 725.6 |
| 500 | 900.0 |
| 2000 | 900.0 |

Table 9 presents optimized heat transfer coefficient for the aluminum/copper interface for 319 3D-wedge model.

TABLE 10

| T (° C.) | HTC (W/m².K) |
|---|---|
| 0 | 325.6 |
| 500 | 50.0 |
| 550 | 900.0 |
| 2000 | 900.0 |

Table 10 presents optimized heat transfer coefficients for the copper/sand interface for 319 3D-wedge model.

TABLE 11

| T (° C.) | HTC (W/m².K) |
|---|---|
| 1 | 500.0 |
| 200 | 491.4 |
| 400 | 702.2 |
| 500 | 1721.9 |
| 570 | 3248.9 |
| 614 | 3270.2 |
| 700 | 5019.4 |
| 2000 | 5019.4 |

Table 11 presents optimized heat transfer coefficients for aluminum/copper for 319 3D-wedge model.

The objective function for all the optimizations is $$S_{ta} = \frac{\sum (T_i^{expt} - T_i^{model})^2}{N}, \tag{23}$$

where $T_i^{expt}$ and $T_i^{model}$ are measured and calculated temperatures at $i^{th}$ time step with a total of N time steps.

There are two sets of unknowns for the optimization problem. One is the temperature dependent heat transfer coefficients and the other the kinetics coefficients. Conducting optimizations for both these sets of variables at the same time is not feasible since the effect of one confound the effect of the other. To de-couple the two sets of unknowns the following two step procedure is adopted.

For determining the heat transfer coefficient for the thermal analysis cup, an optimization is conducted with the heat transfer coefficients as the design variables and $S_{ta}$ as the objective function. An $f_s$ vs. T curve obtained from literature (FIG. 12) is used to provide the latent heat source term in equation 4 instead of the micromodel.

The heat transfer coefficients obtained in the previous step are then used to optimize for the kinetics coefficient using the same objective function $S_{ta}$. This is a three stage optimization process. Region 2 of the cooling curve is used to optimize for $K_p$, region 3 is used to obtain $K_e$ and region 4 is used to obtain $K_c$. For best fit a temperature dependent functional form is used to represent the kinetics coefficients $$K_p = K_{p1}\left(\frac{T - T_{AlSiE}}{T_p - T_{AlSiE}}\right)^{K_{p2}} \tag{24}$$

$$K_e = K_{e1}\left(\frac{T - T_{AlCuE}}{T_{AlSiE} - T_{AlCuE}}\right)^{K_{e2}} \tag{25}$$

$$K_c = \text{Constant} \tag{26}$$

The functional form of $K_p$ and $K_e$ assumes that the kinetics coefficient decreases with temperature. from maximum value to zero between the start and end of transformation temperatures.

Figure 13:
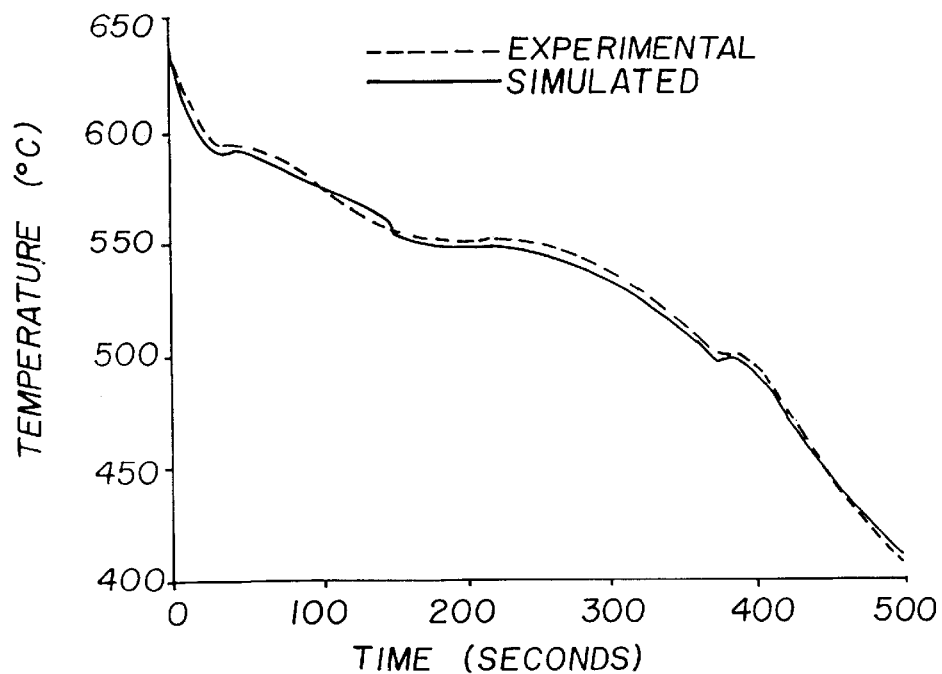
FIG. 13 is a cooling curve for optimized 319 thermal analysis cup.

The results of the optimization are given in Table 12 and FIG. 13.

TABLE 12

| | |
|---|---|
| $K_{p1}$ | = 1.0 × 10⁻⁴ cm/s.(° C.)² |
| $K_{p2}$ | = 2.0 |
| $K_{e1}$ | = 5.0 × 10⁻⁵ cm/s.(° C.)² |
| $K_{e2}$ | = 0.0 |

TABLE 12-continued $K_c = 1.16 \times 10^{-4}$ cm/s.(° C.)$^2$
$a = 1.86$

Figure 14:
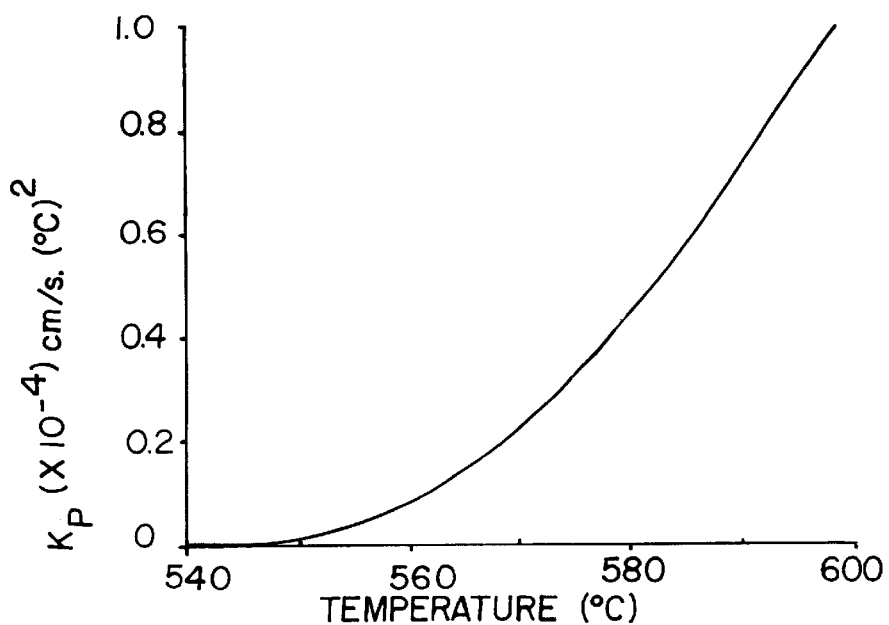
FIG. 14 is a graph showing variation of the primary kinetics coefficient as a function of temperature.
Figure 12:
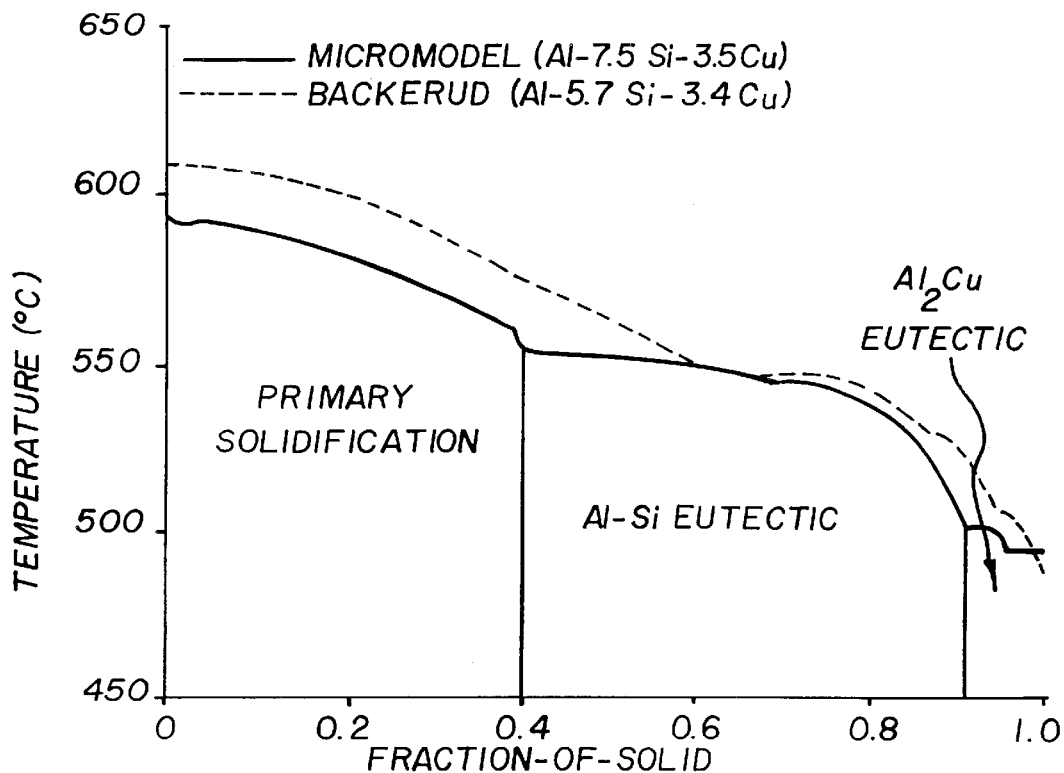
FIG. 12 is a cooling curve showing experimental and simulated fraction solid versus temperature.

The optimum value of exponent $K_{e2}$ turned out to be ≈0. Implying that the eutectic kinetics coefficient is fairly independent of temperature while the primary kinetics coefficient is fairly independent of temperature while the primary kinetics coefficient is significantly dependent on temperature. It is believed to be because the primary solidification takes place over a large range of temperature compared to the eutectic solidification that takes place over a much smaller temperature range. FIG. 14 illustrates the variation of the optimized primary kinetics coefficients with temperature. It shows the variation of primary kinetics coefficient $K_p$ as a function of temperature according to equation 24. FIG. 12 shows a fraction solid curve obtained as a result of the optimized simulation. Regions corresponding to evolution of the primary, eutectic and $Al_2Cu$ phase have been shaded. The simulated fraction solid curve has been compared to the fraction solid curve obtained by Backerud using experimental thermal analysis. The primary solidification in the simulated curve is initiated at a lower temperature and the fraction of primary solid formed is also less than observed in backerud's fraction solid curve. This is due to the fact that the melt chemistry for the simulated fraction solid curve has significantly higher silicon content making it closer to the eutectic composition than Backerud's 319.

Figure 15:
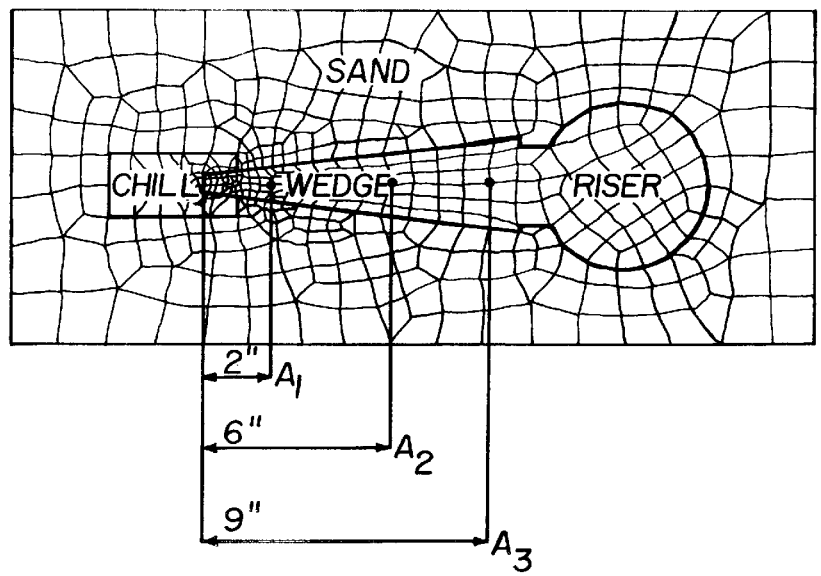
FIG. 15 illustrates a finite element mesh for a section of the wedge casting showing thermocouple locations.

Having calibrated the cup model, the optimized parameters are used to predict the microstructure and cooling curves in a 319 wedge casting. A two-dimensional finite element model of a wedge is first constructed (FIG. 15). The model consists of 449 4-noded quadrilateral elements and 553 nodes. Thermal gradients perpendicular to the cross section in FIG. 15 are considered negligible. This is a reasonable assumption based on the results of simulations using a 3-dimensional model of the wedge.

Heat transfer coefficients for the wedge are obtained using a optimization technique similar to the one described above. Experimental and simulated cooling curves obtained from 3 different points (A1, A2 and A3) of the wedge casting are used for the optimization. FIG. 15 shows the exact locations of these points with respect to the chill. The objective function for the optimization ($S_W$) is defined as follows $$S_W = S_{A1} + S_{A2} + S_{A3} \tag{27}$$

where $$S_{A1} = \frac{\sum (T_{iA1}^{expt} - T_{iA1}^{model})^2}{N} \tag{28}$$

$$S_{A2} = \frac{\sum (T_{iA2}^{expt} - T_{iA2}^{model})^2}{N}, \text{ and}$$

$$S_{A3} = \frac{\sum (T_{iA3}^{expt} - T_{iA3}^{model})^2}{N}$$

Backerud's experimental thermal analysis based $f_s$ vs. T curve (FIG. 12) is used to provide the latent heat generation term for the optimization.

Figure 16:
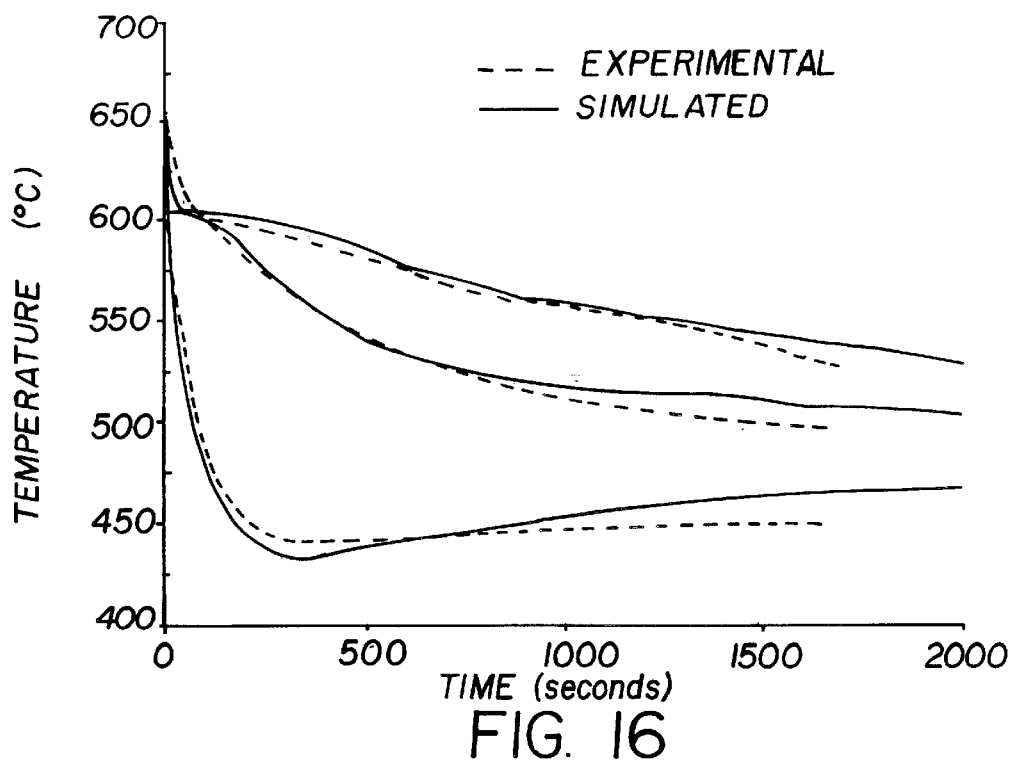
FIG. 16 illustrates experimental and simulated cooling curves for three different regions of a 319 aluminum alloy wedge.
Figure 17:
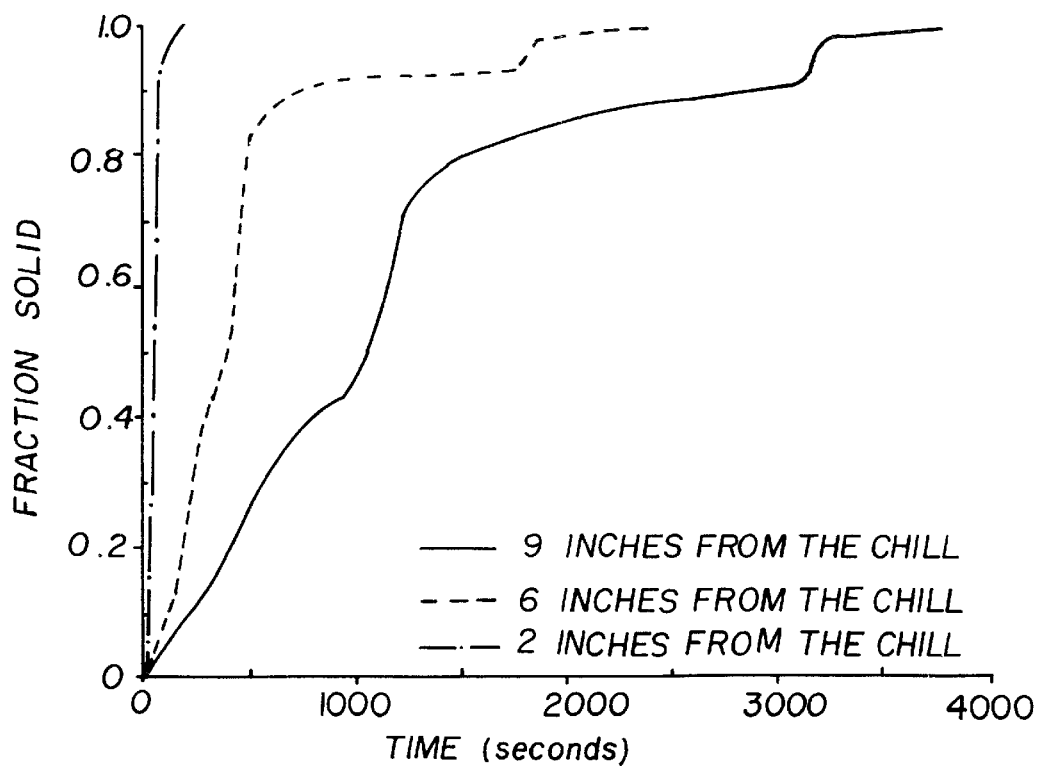
FIG. 17 is a graph illustrating evolution of fraction solid in the wedge.
Figure 18:
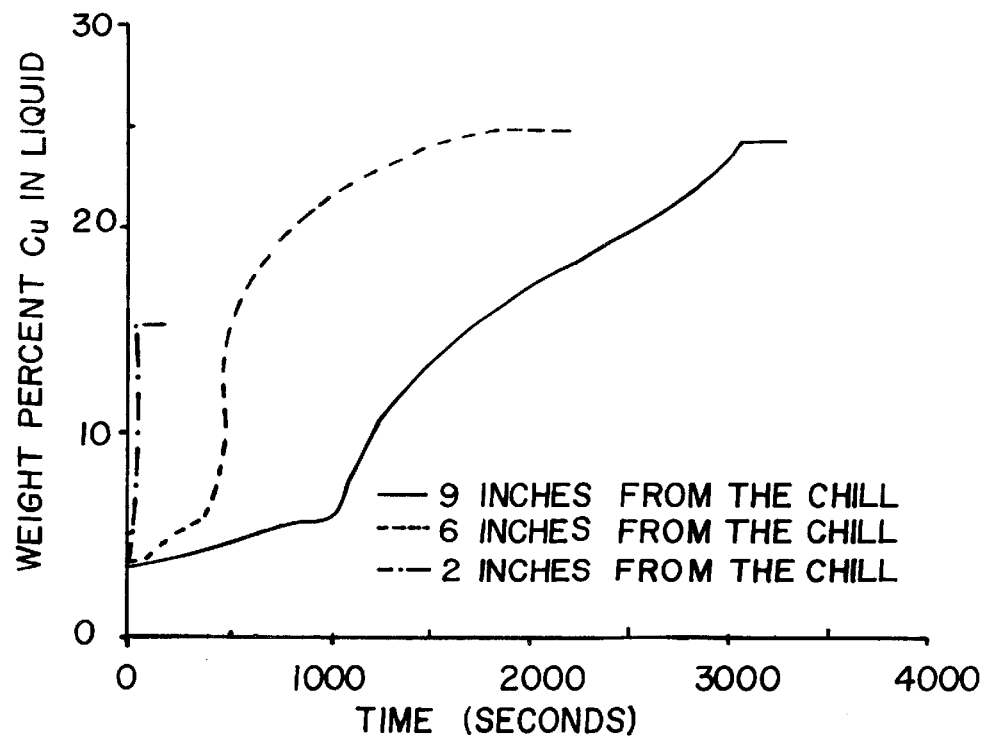
FIG. 18 is a graph illustrating segregation of copper during solidification in the wedge.

Using the heat transfer coefficients obtained from above and optimized kinetics parameters from the cup, the microstructure and cooling curve simulations for the wedge are carried out. FIG. 16 shows experimental and ProCAST simulated cooling curves for points A1, A2 and A3 in the wedge casting. The match between the experimental and simulated cooling curves is good implying that the rate of latent heat generation predicted by the micromodel is reasonable. FIG. 17 plots evolution of fraction solid for the 3 points A1, A2 and A3 in the wedge casting. FIG. 18 shows predicted copper in liquid during solidification. It is seen that for the fast cooling node undercooling are much higher causing the partition coefficient of copper to be higher and segregation of copper liquid to be less than in the slower cooling nodes. This results in lower amount of eutectic $Al_2Cu$ precipitation in the fast cooled region.

Figure 19:
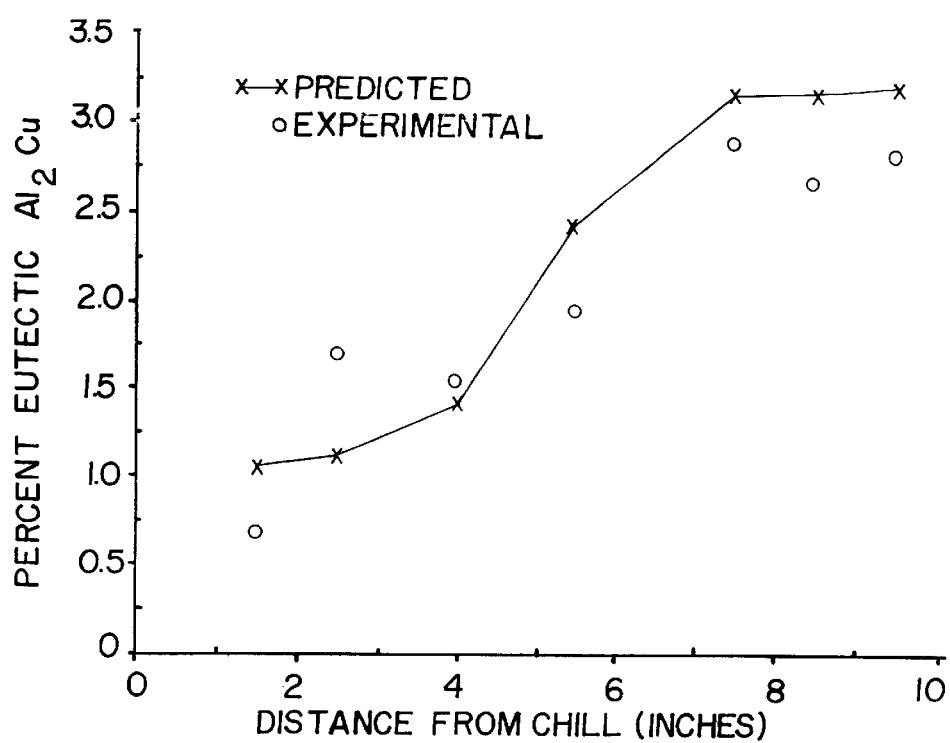
FIG. 19 is a graph comparing observed and simulated fraction of eutectic Al$_2$Cu in the microstructure of the wedge.

FIG. 19 is a plot of the observed and predicted fractions of eutectic $Al_2Cu$ in the as-cast microstructure along the wedge centerline. Although the simulated results are accurate and show similar trends to the observed results, quantitative values of the simulation should not be taken as definitive because there is a degree of uncertainty in the phase diagram data used for the micromodel.

A picture of predicted volume fraction of eutectic $Al_2Cu$ at different regions in a section of the wedge showed simulations in the regions adjacent to the chill were inaccurate because the cooling rates in these regions were quite high and cooling through the entire temperature range of solidification takes less than one time-step. Taking much smaller time-steps solves this problem.

Figure 20:
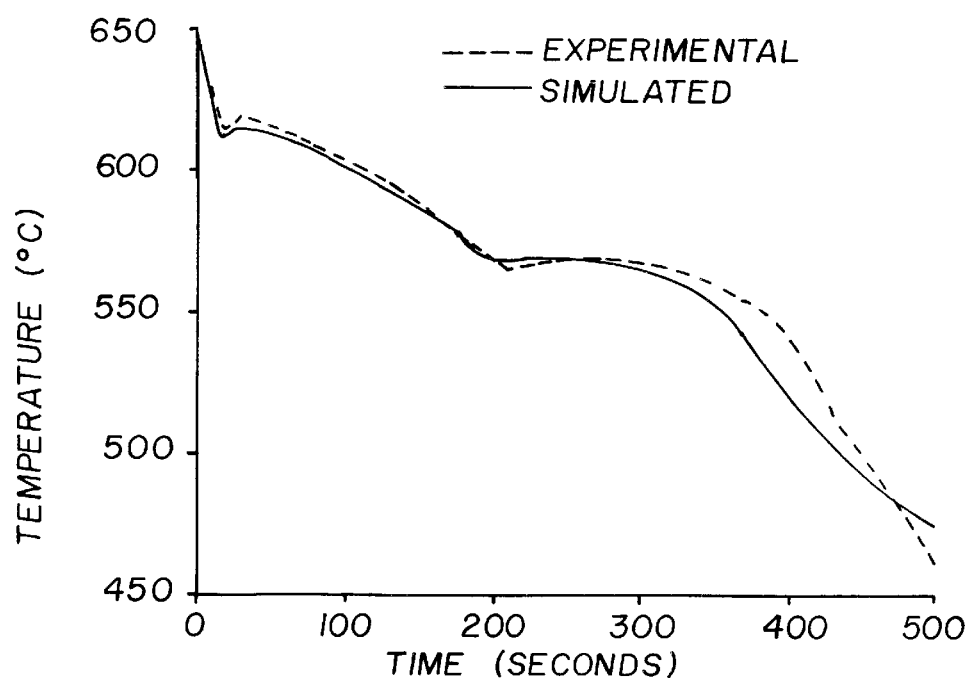
FIG. 20 illustrates experimental and simulated cooling curves for A356 thermal analysis cup.
Figure 21:
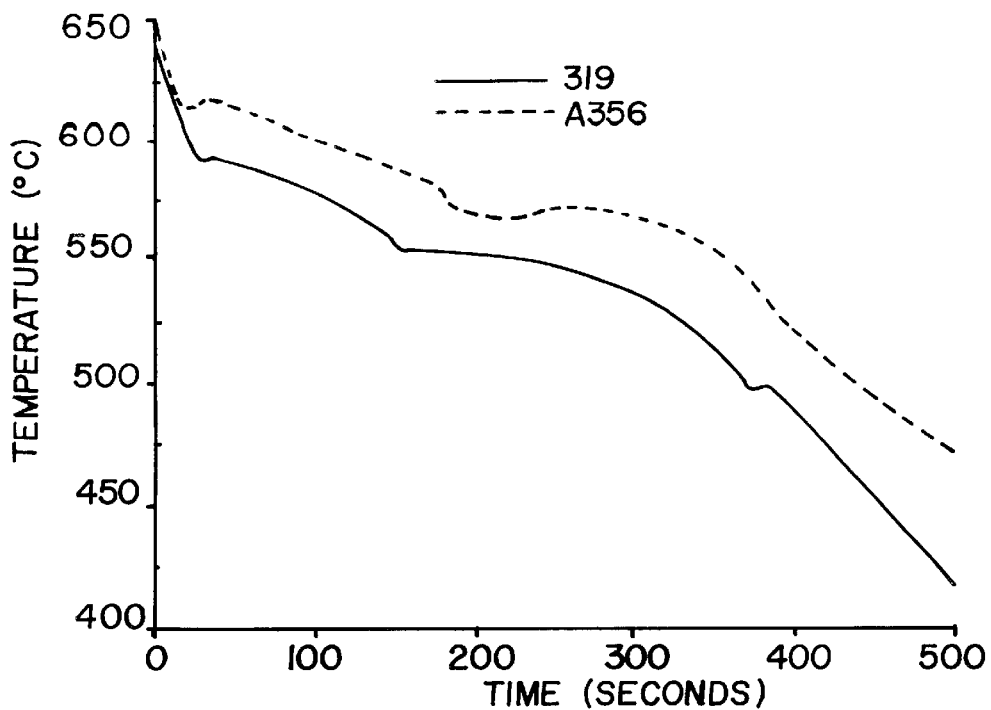
FIG. 21 compares simulated cooling curves for 319 and A356 aluminum alloys.
Figure 22:
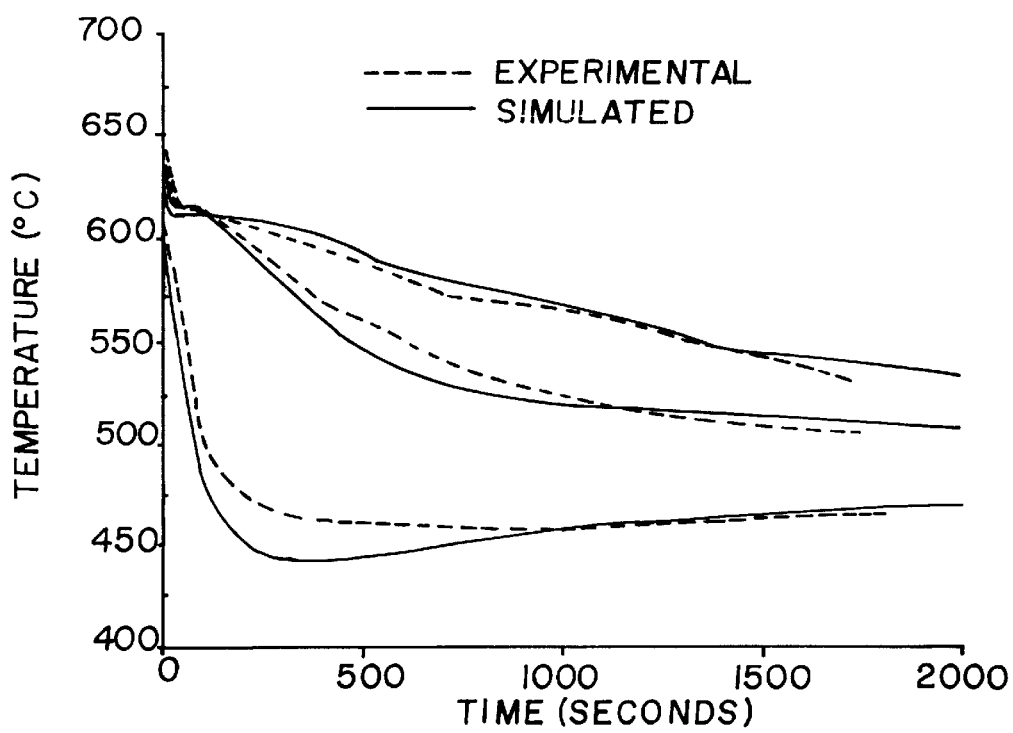
FIG. 22 illustrates experimental and simulated cooling curves for three regions of an A356 wedge.

Except for the copper content, A356 and 319 are similar alloys. The micromodel approach developed for 319 was used to simulate solidification for an A356 alloy. Cooling curves were simulated using the micromodel for a thermal analysis cup and wedge casting. Heat transfer coefficients were obtained using optimization methodologies identical to those used for the 319 cup and wedge. FIG. 20 shows experimental and simulated cooling curves for the thermal analysis cup. FIG. 21 compares micromodel simulated cooling curves for a 319 alloy and an A356 alloy. The micromodel is able to account for changes in liquidus and eutectic temperatures due to local and global variation in the copper composition. The absence of copper accounts for the higher solidification temperatures in A356 (equation 1). The $Al_2Cu$ arrest also missing as expected, in the A356 alloy for the same reason. FIG. 22 shows experimental and predicted cooling curves for the A356 aluminum wedge casting.

The micromodel was used to simulate microstructures and cooling curves in a 3-dimensional model of the same 319 wedge casting described earlier. The model was obtained by extruding the 2-D model in FIG. 15 and it consisted of 6735 elements and 8742 nodes. Heat transfer coefficients presented in Tables 3–11 were obtained using the optimization technique described above.

Figure 23:
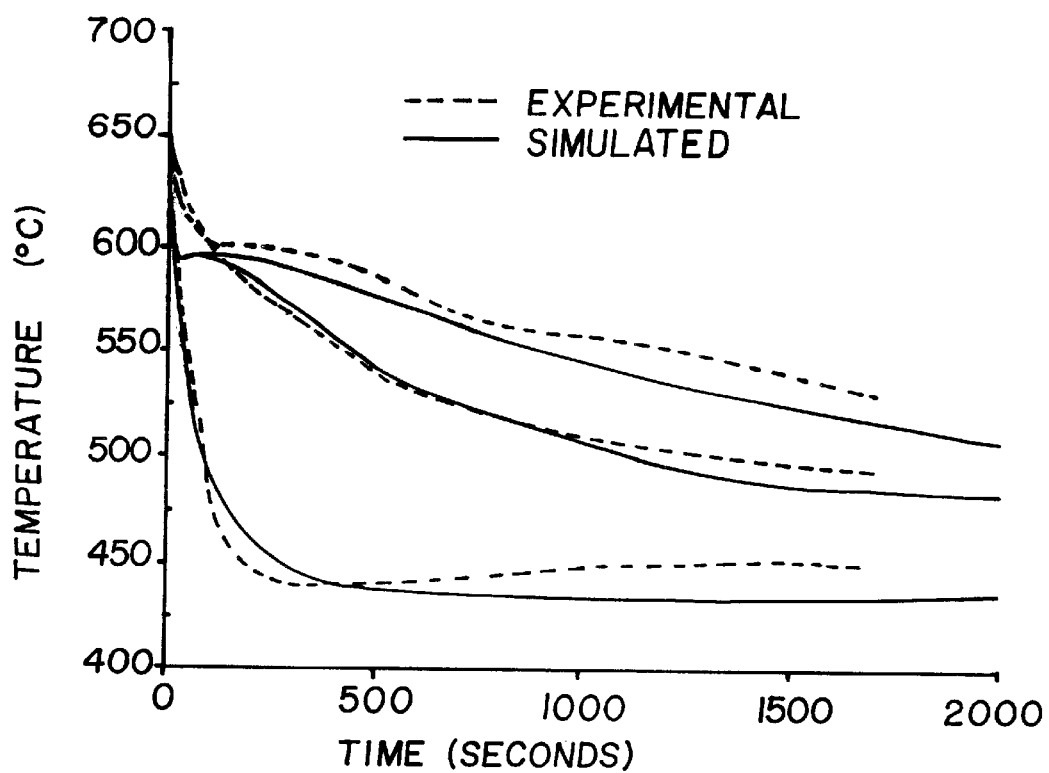
FIG. 23 illustrates experimental and simulated cooling curves for a 3-D model for the 319 wedge.

The results obtained using the 3-D model were consistent with those produced using the 2-D model. FIG. 23 shows experimental and simulated cooling curves using 3-D wedge and the micromodel. Various sections of the wedge model were viewed to observe amounts of $Al_2Cu$. These results once again are consistent with the earlier results showing greater amounts of eutectic $Al_2Cu$ in slower cooling regions. A point to note is that the 3-D model has the ability to predict the microstructure in the casting surface and the core unlike the 2-D model which provides information about a single section of the casting.

A micromodel to simulate microstructure evolution in cast aluminum alloys such as A356, 332, 319 and 206 has been developed. This model has been calibrated using experimental thermal analysis cooling curves and an optimization methodology. The model has then been used to simulate microstructure evolution and cooling curves in a wedge casting. The model is able to predict $Al_2Cu$ precipitation as a function of solidification conditions. A basic principle identified in this investigation is that at low cooling rates, a high degree of segregation of copper in liquid occurs which leads to a high amount of eutectic Al₂Cu. At higher cooling rates the amount of copper available in liquid is less and lower amount of eutectic Al₂Cu is formed.

Micromodeling allows prediction of microstructure as a function of melt chemistry, casting design and other process variables. The objective is to develop a framework for a model to predict as-cast microstructure in 319 and A356. The goal is to use such models for microstructure prediction and ultimately mechanical properties in casting and for casting design of power train components.

Table 13 lists and defines casting process variables used above.

TABLE 13

| | |
|---|---|
| $C^l_{Cu}$ | Concentration of copper in liquid |
| $C^l_{Si}$ | Concentration of silicon in liquid |
| $C^e_{Cu}C^e{cu}$ | Concentration of copper in Al-Al2Cu eutectic |
| $f_l$ | Mass fraction of liquid |
| $f_s$ | Mass fraction of solid |
| $f_c$ | Mass fraction of the copper eutectic |
| $f^{max}_c$ | Maximum mass fraction of the copper eutectic that can be formed |
| $k_{cu}$ | Partition coefficient of copper in aluminum |
| $k_{si}$ | Partition coefficient of silicon in aluminum |
| $K_i$ | Kinetics coefficients for evolution of phase i |
| $K_p$ | Kinetics coefficients for evolution of primary phase |
| $K_e$ | Kinetics coefficients for evolution of eutectic phase |
| $K_c$ | Kinetics coefficients for evolution of ternary phase |
| n (t) | Number of grains |
| $n_p$ | Number of grains of the primary phase |
| $n_e$ | Number of grains of the eutectic phase |
| $n_c$ | Number of grains of the ternary eutectic |
| $R_i$ | Grain radius |
| $\Psi(V_s)$ | Grain impingement function |
| $\Delta T$ | Undercooling |
| $\Delta T_p$ | Undercooling with respect to the aluminum liquidus |
| $\Delta T_e$ | Undercooling with respect to the aluminum-silicon eutectic |
| $\Delta T_c$ | Undercooling with respect to the ternary eutectic |
| $T_{AlL}$ | Aluminuin liquidus |
| $T_{AlSiE}$ | Aluminum-silicon eutectic |
| $V_i$ | Volume fraction of phase i |
| $V_p$ | Volume fraction of primary phase |
| $V_i$ | Volume fraction of eutectic phase |
| $V_c$ | Volume fraction of Ternary eutectic |

What is claimed is:

1. A method for quantitatively predicting and consequently minimizing amount of eutectic Al₂Cu formed during solidification of Al—Si—Cu alloys used in cast aluminum alloy components, comprising the steps of:

developing micromodel to simulate microstructure evolution in A356, 332, 319 and 206 cast aluminum alloys;

calibrating the micromodel using experimental thermal analysis cooling curves and an optimization process;

simulating microstructure evolution and cooling curves in a casting using the calibrated micromodel; and predicting Al₂Cu precipitation in the casting as a function of solidification conditions.

2. The method of claim 1 including the step of optimizing casting process conditions for optimal tensile properties using said micromodel.

3. A method for quantitatively predicting and consequently minimizing amount of eutectic Al₂Cu formed during solidification of Al—Si—Cu alloys used in cast aluminum alloy components, comprising the steps of:

developing micromodel to simulate microstructure evolution in cast aluminum alloys, said micromodel developing step including developing a kinetics model according to the relationship $$\frac{dV_i}{dt} = (K_i(V_i))^{\frac{2}{3}}(n)^{\frac{1}{3}}\Delta T_i^2(\Psi(V_s)),$$

where kinetics coefficient for evolution of phase i, $$K_i=(4\pi)^{1/3}(3)^{2/3}\mu_i,$$

$\mu_i$ is growth kinetics coefficient for phase i, $V_s$ is instantaneous volume fraction solid, and grain impingement function $\Psi=(1-V_s)^a$;

calibrating the micromodel using experimental thermal analysis cooling curves and an optimization process;

simulating microstructure evolution and cooling curves in a casting using the calibrated micromodel; and predicting Al₂Cu precipitation in the casting as a function of solidification conditions.

4. A method for quantitatively predicting and consequently minimizing amount of eutectic Al₂Cu formed during solidification of Al—Si—Cu alloys used in cast aluminum alloy components, comprising the steps of:

developing micromodel to simulate microstructure evolution in cast aluminum alloys;

calibrating the micromodel using experimental thermal analysis cooling curves and an optimization process;

simulating microstructure evolution and cooling curves in a casting using the calibrated micromodel;

predicting Al₂Cu precipitation in the casting as a function of solidification conditions; and calibrating said micromodel using cooling curves from thermal analysis cups according to an objective function $$ta = \frac{\sum (T_i^{expt} - T_i^{model})^2}{N},$$

where $T_i^{expt}$ and $T_i^{model}$ are measured and calculated temperatures, respectively, at $i^{th}$ time step with a total of N time steps.

5. The method of claim 4 including the step of determining initial values of variables in said micromodel.

6. The method of claim 4 including the step of determining heat transfer coefficients for the thermal cup analysis using the heat transfer coefficients as design variables and $S_{ta}$ as the objective function.

7. The method of claim 6 including the step of determining kinetics coefficients using said heat transfer coefficients.

8. The method of claim 7 including the step of representing the kinetics coefficients using temperature dependent functional forms $$K_p = \left(K_{pl}\left(\frac{T - T_{AlSiE}}{T_p - T_{AlSiE}}\right)\right)^{K_{p2}},$$

$$K_e = K_{el}\left(\frac{T - T_{AlCuE}}{T_{AlSiE} - T_{AlCuE}}\right)^{K_{e2}}, \text{ and}$$

$$K_c = \text{Constant,}$$

where $K_e$ is kinetics coefficient for evolution of eutectic phase,
$K_p$ is kinetics coefficient for evolution of primary phase,
$K_c$ is kinetics coefficient for evolution of ternary phase,
T is undercooling,
$T_{AlL}$ is aluminum liquidus, and
$T_{AlSiE}$ is aluminum-silicon eutectic.

9. A method for quantitatively predicting and consequently minimizing amount of eutectic $Al_2Cu$ formed during solidification of Al—Si—Cu alloys used in a structural component, comprising the steps of:

forming a mold having a chill;
pouring a wedge casting;
analyzing test samples from the wedge casting and determining physical, chemical and metallurgical properties of the wedge casting;
constructing kinetic and solute redistribution models using metallagraphic data from the analysis of the test samples and Al—Si—Cu ternary phase diagram derived from the analysis of the test samples;
determining area fraction $Al_2Cu$ of said test samples;
approximating aluminum liquidus temperature ($T_{AlL}$) and Al—Si eutectic temperature ($T_{AlSiE}$);
obtaining ternary eutectic temperature ($T_T$) from cooling curves produced using test data from the analysis;
determining partition coefficients ($k_{cu}$, $k_{si}$); and
predicting $Al_2Cu$ precipitation in the wedge casting as a function of solidification conditions.

10. The method of claim 9 including the step of developing a kinetic model representing both primary and eutectic growth.

11. The method of claim 10 wherein said kinetic model may be expressed mathematically as:

$$\frac{dV_i}{dt} = (K_i(V_i))^{\frac{2}{3}}(n)^{\frac{1}{3}}\Delta T_i^2(\Psi(V_s)),$$

$\mu_i$=growth kinetics coefficient for phase i,
$V_s$=instantaneous volume fraction solid, and
$\Psi=(1-V_s)^a$.

12. The method of claim 9 including the step of estimating microsegregation of alloy elements using Scheil type equation assuming there is no back diffusion in solid while liquid is completely mixed.

13. The method of claim 9 including the steps of:
determining mass fraction of eutectic;
determining mass fraction of $Al_2Cu$ and converting to volume fraction; and
determining phase transformation temperatures and partition coefficients.

14. The method of claim 9 including the step of forming a mathematical model of said casting using mechanical and physical properties of said test samples, said mathematical model.

15. The method of claim 9 including the step of developing equations to represent growth kinetics of various phases as a function of undercooling.

16. The method of claim 9 including the step of developing solute redistribution models to track local concentrations of Si an Cu as solidification proceeds.

17. The method of claim 9 including the step of calibrating said mathematical model using thermal analysis cups according to an objective function $$S_{ta} = \frac{\sum (T_i^{expt} - T_i^{model})^2}{N};$$

solving the calibrated mathematical model for initial values of variables; and
using the initial values of variables to predict microstructure and cooling curves for a casting.

18. A method for controlling mechanical and physical properties of cast aluminum alloy components, comprising the steps of:
developing micromodel to simulate microstructure evolution in cast aluminum alloy;
developing a kinetic model representing both primary and eutectic growth;
calibrating the micromodel using experimental thermal analysis cooling curves and an optimization process;
simulating microstructure evolution and cooling curves in a casting using the calibrated micromodel; and
optimizing the casting process conditions for optimal tensile properties using the micromodel.

19. The method of claim 18 including the step of developing a kinetic model representing both primary and eutectic growth.

* * * * *